US009586871B2

(12) United States Patent
Sabin

(10) Patent No.: US 9,586,871 B2
(45) Date of Patent: Mar. 7, 2017

(54) POTENTIATION OF FIXED COPPERS AND OTHER PESTICIDES CONTAINING COPPER AND SUPPLEMENTING PLANT NUTRITION

(71) Applicant: Robert Sabin, Mill Neck, NY (US)

(72) Inventor: Robert Sabin, Mill Neck, NY (US)

( * ) Notice: Subject to any disclaimer, the term of this patent is extended or adjusted under 35 U.S.C. 154(b) by 0 days.

(21) Appl. No.: 15/005,969

(22) Filed: Jan. 25, 2016

(65) Prior Publication Data

US 2016/0137564 A1   May 19, 2016

Related U.S. Application Data

(63) Continuation-in-part of application No. 14/689,675, filed on Apr. 17, 2015, now Pat. No. 9,271,502, which is a continuation-in-part of application No. 14/674,607, filed on Mar. 31, 2015, which is a continuation-in-part of application No. 14/625,405, filed on Feb. 18, 2015, now Pat. No. 9,247,734.

(60) Provisional application No. 62/094,775, filed on Dec. 19, 2014, provisional application No. 62/021,819, filed on Jul. 8, 2014, provisional application No. 62/020,247, filed on Jul. 2, 2014, provisional application No. 62/003,528, filed on May 27, 2014, provisional application No. 62/002,330, filed on May 23, 2014.

(51) Int. Cl.
| | | |
|---|---|---|
| *A01N 59/16* | (2006.01) | |
| *A01N 59/20* | (2006.01) | |
| *C05G 3/02* | (2006.01) | |
| *C05D 9/02* | (2006.01) | |

(52) U.S. Cl.
CPC .............. *C05G 3/02* (2013.01); *A01N 59/20* (2013.01); *C05D 9/02* (2013.01)

(58) Field of Classification Search
None
See application file for complete search history.

(56) References Cited

U.S. PATENT DOCUMENTS

| | | | |
|---|---|---|---|
| 2,051,910 | A | 8/1936 | Sessions |
| 3,046,188 | A | 7/1962 | Gaudian et al. |
| 3,086,908 | A | 4/1963 | Telle et al. |
| 3,231,464 | A | 1/1966 | Dettwiler et al. |
| 4,857,322 | A | 8/1989 | Goettsche et al. |
| 5,202,353 | A | 4/1993 | Schroth et al. |
| 5,385,934 | A | 1/1995 | Schroth et al. |
| 5,637,258 | A | 6/1997 | Goldburt et al. |
| 6,036,886 | A | 3/2000 | Chhabra et al. |
| 6,146,606 | A | 11/2000 | Atobe et al. |
| 6,294,274 | B1 | 9/2001 | Kawazoe et al. |
| 6,372,238 | B1 * | 4/2002 | Rajamannan ........ A01N 25/34 424/405 |
| 6,399,838 | B1 | 6/2002 | Li et al. |
| 6,562,757 | B1 | 5/2003 | Ferrier et al. |
| 6,843,830 | B2 * | 1/2005 | Sherer .................. B01D 53/04 423/210 |
| 7,105,136 | B2 | 9/2006 | Ploss et al. |
| 7,402,296 | B2 | 7/2008 | Oberholzer |
| 7,449,196 | B2 | 11/2008 | Sabin |
| 8,192,766 | B2 | 6/2012 | Martinez et al. |
| 8,193,119 | B2 | 6/2012 | Fabry et al. |
| 8,207,089 | B1 | 6/2012 | Fabry |
| 8,216,972 | B1 | 7/2012 | Fabry et al. |
| 8,221,791 | B1 | 7/2012 | Santra |
| 8,409,627 | B2 | 4/2013 | Richardson et al. |
| 8,461,079 | B1 | 6/2013 | Fabry |
| 8,618,149 | B2 | 12/2013 | Melander et al. |
| 8,623,220 | B2 | 1/2014 | Bagabas et al. |
| 8,795,736 | B2 | 8/2014 | Huber |
| 2012/0316220 | A1 | 12/2012 | Ward et al. |
| 2013/0189364 | A1 | 7/2013 | Sabin |
| 2013/0225406 | A1 | 8/2013 | Borges Rodriguez et al. |
| 2014/0023691 | A1 | 1/2014 | Melander et al. |

FOREIGN PATENT DOCUMENTS

| | | | |
|---|---|---|---|
| CN | 101643772 | * | 2/2010 |
| GB | 1092383 | * | 11/1964 |
| GB | 1074159 | * | 6/1967 |
| WO | 2011033040 A2 | | 3/2011 |

(Continued)

OTHER PUBLICATIONS

Ji et al.(Effects and mechanism of copper and zinc elements on controlling fusarium-wilt disease of banana, Yuanyi Xuebao, 2012, 39(6), 1064-72).*
Qi et al.(Inactivation effect of 10 compounds on *Fusarium oxysporum* f. sp. cubense and its toxin, Guoshu Xuebao, 2008, 25(1), 78-82).*
Sanjeev et al.(Efficacy of micro nutrients on Fusarium wilt( *Fusarium oxysporum* f. sp. cubense) and its synergistic action with Trichoderma viride, Notulae Botanicae Horti Agrobotanici Cluj-Napoca, 2008, 36(1), 52-54).*
Dope chemical defin-Bing, 4/1516.*
Michael Eshed et al, "A Zn-Doped CuO Nanocomposite Shows Enhanced Antibiofilm and Antibacterial Activities Against *Streptococcus* Mutans Compared to Nanosized CuO"; 2013; 9 pages; Advanced Functional Materials; www.afm-journal.de; www.MaterialsViews.com.

(Continued)

*Primary Examiner* — Alton Pryor
(74) *Attorney, Agent, or Firm* — Alfred M. Walker; Jennifer Yancy

(57) ABSTRACT

A pesticide composition includes at least one biologically inert carrier; and at least one ferrite or at least one doped component including at least one fixed copper compound doped with at least one compound selected from the group consisting of iron compounds, zinc compounds, magnesium compounds, calcium compounds, and combinations and/or mixtures thereof. In one embodiment, the doped component has a particle size of about 0.5 nm to about 30 microns. A method for the control of pests includes the step of applying to the pests or their growth habitat the aforementioned composition. The method also includes the control of fungal and other diseases in banana plants, by applying the aforementioned composition to their growth habitat in banana plant groves.

18 Claims, 4 Drawing Sheets

(56) References Cited

FOREIGN PATENT DOCUMENTS

| WO | 2013148677 A1 | 10/2013 |
|---|---|---|
| WO | PCT2014181329 A1 | 11/2014 |
| WO | PCTUS2015031702 A1 | 5/2015 |

OTHER PUBLICATIONS

Eyal Malka et al; "Eradication of Multi-Drug Resistant Bacteria by a Novel Zn-doped CuO Nanocomposite"; 2013; 8 pages; www.small-journal.com.

Rob Ramaker, Search for a better banana, Science, Jan. 7, 2016. 3 pages, https://resource.wageningenur.nl/en/show/Searching-for-a-better-banana.htm.

Nordox, vemo (TM) FG, Cu30+Zn30, Foliar Fertilisers, 4 pages.

Jim Graham, Integrated Management of Root Health of HLB-Affected Trees and Canker in Grapefruit, Florida Citrus Show, Jan. 24, 2013; University of Florida IFAS Citrus Research and Education Center; 34 pages.

Jim Graham, Novel Bactericides and Application Methods to Control Huanglongbing (HLB) Disease of Citrus, IV International Symposium of Plant-Pathogenic Bacteria, Guadalajara, Jalisco, Mexico; University of Florida IFAS; 33 pages.

Cocco, Arturo; Hoy, Marjorie A.Toxicity of Organosilicone Adjuvants and Selected Pesticides to the Asian Citrus Psyllid (Hemiptera: Psyllidae) and its Parasitoid Tamarixia Radiata (Hymenoptera: Eulophidae), Florida Entomologist;2008, vol. 91 Issue 4, p. 619, Source: Academic Journal 3 pages.

Fact Sheet, Citrus Diseases Huanglongbing (HLB), http://idtools.org/id/citrus/diseases/factsheet.php?name=Huanglongbing+(HLB), 3 pages.

Joe Satran, Citrus Greening Forces Florida Growers to Trust a Controversial Savior; posted Aug. 30, 2013; updated Nov. 11, 2013, 14 pages.

T.R. Gottwald; J.H. Graham; M.S. Irey; T.G. McCollum; and B.W. Wood; Inconsequential Effect of Nutritional Treatments on Huanglongbing Control, Fruit Quality, Bacterial Titer and Disease Progress; revised Dec. 20, 2011—accepted Jan. 11, 2012; published by Elsevier Ltd, www.elsevier.com/locate/cropro; 5 pages.

E.E. Grafton-Cardwell, Entromology, UC Riverside/Kearney Agricultural Center, Parlier; M.P. Daugherty, Entomology, UC Riverside; Pest Notes: Asian Citrus Psyllid and Huanglongbing Disease; produced by University of California Statewide IPM Program, 6 pages; University of California Agricultur and Natural Resources; http://www.ipm.ucdavis.edu/PMG/PESTNOTES/pn74155.html.

MOMENTIVE—Silwet Adjuvants and SAF Antifoams for Agricultural Applications; MOMENTIVE, 22 Corporate Woods Boulevard, Albany, NY 12211; momentive.com; 8 pages.

Sulvaris; Plant Nutrient Sulphur Deficiencies, sulphur in agriculture; Sulvaris, 6443 2nd Street S.E., Calgary, Alberta, Canada T2H 1J5; info@sulvaris.com, 403-259-4777 phone; 403-259-4788 FAX; 4 pages.

Zinc hydroxide—Wikipedia, the free encyclopedia; http://en.wikipedia.org/wiki/Zinc_hydroxide; 4 pages.

Zinc sulfate from Wikipedia, the free encyclopedia; 3 pages.

K.C. Anyaogu; and A. V. Fedorov; D.C. Neckers Center for Photochemical Sciences, Bowling Green State University, Bowling Green Ohio 43403; research article, Synthesis, Characterization, and Antifouling Potential of Functionalized Copper Nanoparticles; Langmuir 2008, 24 (8), pp. 4340-4346; published Mar. 15, 2008; 2 pages.

G. Borkow, and J. Gabbay; PubMed Abstract, Copper as a Biocidal Tool; Curr Med Chem 2005;12(18):2163-75; http://www.ncbi.nlm.nih.gov/pubmed/16101497; 2 pages.

I. Capek, Preparation of Metal Nanoparticles in Water-in-Oil (w/o) Microemulsions; doi:10.1016/j.cis.2004.02.003; Advances in Colloid and Interface Science; vol. 110; Issues 1-2; Jun. 30, 2014, pp. 49-74; Elsevier B.V.; FAX +42-7-375923; 1 page.

M.H. Freeman and C.R. McIntyre; Abstract: A Comprehensive Review of Copper-Based Wood Preservatives with a focus on new micronized or dispersed copper systems; received for publication Aug. 2008; Article No. 10523; 22 pages.

H.L. Karlsson, P. Cronholm, J. Gustafsson and L. Moller; Abstract: Copper Oxide Nanoparticles are Highly Toxic: A Comparison Between Metal Oxide Nanoparticles and Carbon Nanotubes; Chem Res Toxicol, Sep. 2008:21(9):1726-32. doi: 10.1021/tx800064j. Epub Aug. 19, 2008; PMID: 18710264 [PubMed—indexed for MEDLINE]; 3 pages.

E.C. Large; article first published online: Feb. 26, 2008; Field Trials of Copper Fungicides for the Control of Potato Blight I. Foliage Protection and Yield; Annals of Applied Biology, vol. 32, Issue 4; pp. 319-329, Nov. 1945; http://www.altmetric.com/details.php?domain=onlinelibrary.wiley.com&doi=10.1111/j.1744-7348.1945.tb026263.x; 2 pages.

Maniprasad, Pavitra, Santra and Swadeshmukul; Novel Copper (Cu) Loaded Core-Shell Silica Nanoparticles with Improved Cu Bioavailability: Synthesis, Characterization and Study of Antibacterial Properties; Journal of Biomedical Nanotechnology, vol. 8, No. 4, Aug. 2012, pp. 558-566(9); American Scientific Publishers; 2 pages.

Synthesis of Copper Nanoparticles in Nonionic Water-in-Oil Microemulsions, Department of Chemistry, Peking University, Beijing 100871 People's Republic of China, Received Jul. 15, 1996, accepted Oct. 14, 1996; Article No. CS964647, Journal of Colloid and Interface Science 186, 498-500 (1997), 3 pages.

T. Theivasanthi and M. Alagar, Studies of Copper Nanoparticles Effects on Micro-organisms, Centre for Research and P.G. Dept. of Physics, Ayya Nadar Janaki Ammal College, Sivakasi-626124, Tamilnadu, India, E-mail: theivasanthi@pacrpoly.org, 6 pages.

K. Zhang, C.H. Chew, G.Q. Xu, J. Wang and L.M. Gan, Synthesis and Characterization of Silica-Copper Oxide Composite Derived from Microemulsion Processing, Department of Chemistry, National University of Singapore, Republic of Singapore, Langmuir, published Apr. 2, 1999; http://pubs.acs.org/doi/abs/10.1021/1a9811158?journalCode=Langd5, 2 pages.

Bayer CropScience Safety Data Sheet, Blue Shield DF Copper Fungicide, Version 1/AUS, print and revision date Apr. 7, 2013; 8 pages.

Rader's chem4kids.com, Matter: Mixtures; http://www,chem4kids.com/files/matter_mixture.html; 3 pages.

Chemicool; Cooler Than Absolute Zero!; Definition of Mixture—Chemistry Dictionary; http://www.chemicool.com/definition/mixture.html; 2 pages.

Mixture/Define Mixture at Dictionary.com; http://dictionary.reference.com/browse/mixture; 2 pages.

Medical Term: Mixture definition; Drugs.com; http://www.drugs.com/dict/mixture.html; 1 page.

Du Pont Material Safety Data Sheet; :KOCIDE 101 Fungicide/Bactericide; revised Apr. 12, 2007, printed Apr. 13, 2007; 10 pages.

Eldorado Chemical; Roles of the 16 Essential Nutrients in Crop Development; http://www.eldoradochemical.com/fertiliz1.htm; 4 pages.

GCSE Chemistry, What is a Mixture?—What is the Definition of a Mixture? . . . ; Elements, Compounds and Mixtures; http://www.gcsescience.com/e4-mixture-separation.htm; 2 pages.

Liquid Copper Product Characteristics and MSDS details, C mfg. Suntec NZ Ltd, 747 Makerua Rd. , P.O. Box 41, (SH57), Tokomaru 4864, New Zealand, +64 6 3298142, Fax +64 6 3298041; internet www:suntec.co.nz; email: suntec@suntec.co.nz; Apr. 2012; 2 pages.

Material Safety Data Sheet #16047-12-LP1; Copper Hydroxide; Coppercide PCP#16047; mfg. Loveland Products Canada, Inc., 789 Donnybrook Drive, Dorchester, Ontario NOL, 1G5; 1-800-561-8273 or Chemtrec 1-800-424-9300; issued Sep. 12, 2012; 3 pages.

Plant Nutrients; http://www.ncagr.gov/cyber/kidswrld/plant/nutrient.htm; 6 pages.

Material Safety Data Sheet; Champion Wettable Powder; Doc #070NM; Nufarm Agriculture (Pty) Ltd, PO Box 165, Malelane, 1320, South Africa; (013)3962233; FAX (011) 3964666; email: technical@villacrop.com; effective date Jul. 2002 Rev. 1 800 88 8099; 1; 5 pages.

Material Safety Data Sheet, Copper Hydroxide 77.0% WP; Nufarm Malaysia SDN BHD, L2.03 Wisma BU8, No. 11, Lebuh Bandar

(56) References Cited

OTHER PUBLICATIONS

Utama, Bandar Utama, 47800, Petaling, Jaya, Selangor D.E., Malaysia; +60 3 7629 7233, FAX +60 3 7629 7229; email salesmy@my.nufarm.com; Issued Aug. 1, 2001; 5 pages.
Pan Pesticides Database—Pesticide Products; Citation: Keley, S.E; Hill, B.R.; Omre, S.; Choi, A.H.; Pesticide Action Network, North America (Oakland, CA,; http://www.pesticideinfo.org/List_Products.jsp?Rec_Id=PC335248,Chem_Name=Copper% . . . ; 5 pages.
Material Safety Data Sheet, Ridomil Gold Copper; Syngenta Crop Protection, Inc. P.O. Box 18300, Greensboro, NC 27419; 1-800-888-8372; Revised Feb. 26, 2007, replaces Jun. 5, 2006; 6 pages.
Anne Marie Helmenstine, Ph.D; What Is a Mixture? About.com Chemistry; http://chemistry.about.com/od/lecturenotes13/f/What-Is-A-Mixture.htm; 1 page.
What is a Mixture in Chemistry?; http://www.ask.com/question/what-is-a-mixture-in-chemistry; 2 pages.
What is the scientific definition of a mixture?; http://wiki.answers.com/Q/What_is_the_scientific_definition_of_a_mixture; 3 pages.
Mixture From Wikipedia, the free encyclopedia; revised Apr. 10, 2014; 4 pages.
Mixture; www.wow.com/Mixture; Based on the Random House Dictionary 2014; http://dictionary.reference.com/browse/mixture; 2 pages.
Agro News; Italian Government Urged to Take Action to Fight Against Olive Tree Epidemic; Jan. 9, 2015; http://news.agropages.com/News/NewsDetail—13932-e.htm; 3 pages.
Daily Mail.com; Olive Oil Under Threat From Bacteria Whis is Hitting Hundres of Thoursands of Trees in Italy—and could set prices soaring; updated and published Aug. 15, 2014; http://www.dailymail.co.uk/news/article-27276119/Olive-oil-threat-bacteria-hitting-hundred . . . ; 2 pages.
Lizette Alvarez; The New York Times; Citrus Disease With No Cure Is Ravaging Florida Groves; published May 8, 2013; 4 pages.
Joe Satran; Citrus Greening Forces Florida Growers to Trust a Controversial Savior; http://www.hufffingtonpost.com/2013/08/30/citrus-greening_n_3780984.html; posted Aug. 30, 2013 and updated Nov. 11, 2103; 14 pages.
Tim Spann; Overview of Citrust Grower Nutritional Spray Compositions; University of Florida, IFAS, Citrus Research and Education Center; International Citrus and Beverage Conference, Clearwater Beach, FL; Sep. 16, 2011; 26 pages.
J.D. Janse and A. Obradovic; MiniReview, Xylella Fastidiosa: Its Biology, Diagnosis, Control and Risks; Dept. of Lab Methods/Diagnostics, Dutch General Inspection Service, PO Box 1115, 8300 BC Emmeloord, The Netherlands, Plant Pathology Dept., University of Belgrade, Serbia; E-mail: jjanse@nak.nl; FAX +31.527.635411; Journal of Plant Pathology (2010);14 pages.
Definition of Complex-Chemistry Dictionary; Chemicool—Cooler Than Absolute Zero;http://www.chemicool.com/definition/complex.html; 2 pages.
Uses of Copper Compounds: Table B—Plant Diseases Amenable to Control by Copper Fungicides; Copper Development Association Inc.; A Copper Alliance (http://copperalliance.org) Member; http://www.copper.org/resources/properties/compounds/table b. html; 11 pages.
Diffen—Compound vs. Element; http://www.diffen.com/difference/Compound_vs_Element; 5 pages.
X. Mourichon et al,in collaboration with the PROMUSA Sigatoka Working Group, Sigatoka Leaf Spot Diseases, Musa Disease Fact Sheet No. 8, International Network for the Improvement of Banana and Plantain, Parc Scientifique Agropolis II, 34397 Montpellier Cedex 5, France, Tel: 33-(0)4 67 61 13 02, Fax: 33-(0)4 67 61 03 34, e-mail: nibap@cgnet.com, Oct. 1997, 4 pages, http://www.cgiar.org/ipgri/lnibap/.
Rob Ramaker, Social Sciences, Banana Disease Continues to Spread, Science, Nov. 26, 2015, 3 pages, http://resource.wageningenur.nl/en/science/show/Banana-disease-continues-to-spread.htm.
Dr. Terry Mabbett, Focus on Agriculture, Copper Completes the Circle for Sigatoka Control, Focus on Agriculture, Jul./Aug. 2014, 4 pages, www.international-pest-control.com.
R.S. Bennett et al of Cornell University, Black Sigatoka of Bananas and Plantains, 2003, 11 pages, www.apsnet.org/edcenter/lntropp/lessons/fungi/ascomycetes/Pages/BlackSigatoka.aspx.
Wageningen UR for Quality of Life, Dossier, Banana Cultivation, Nov. 19, 2015, 3 pages, Contact form (/en/Dossiers/file/Banana-cultivation.htm? contactpersonid=3603&presentationid=399132).
Randy Ploetz, Tropical Research & Education Center, University of Florida,USA discusses the management of the most important disease of banana and plantain, Black Sigatoka, Pesticide Outlook—Feb. 2000, 5 pages, The Royal Society of Chemistry 2000 Journal.
Queensland Government, Black Sigatoka, Plant Health Australia Fact Sheet, 2 Pages, Exotic Plant Pest Hotline 1-800-084-881.
Manly P. Hall, The Talented Mr Putin, Bananageddon: Millions Face Hunger as Deadly Fungus Panama Disease Decimates Global Banana Crop, Outrageous Minds—Alternative News Lanatic Fringe Esoteric, Apr. 6, 2014, 5 pages, https://outrageousminds.wordpress.com.
Douglas H. Marin et al, Black Sigatoka: An Increasing Threat to Banana Cultivation, Publication No. D-2003-0110-01F, 2003 The American Phytopathological Society, 15 pages, Plant Disease/vol. 87 No. 3.
Randy Ploetz, Tropical Research and Education Center, University, IFAS, Homestead, Black Sigatoka of Banana: the most important disease of a most important fruit, APS Publications APS Features, 2001, 6 pages, https://www.apsnet.org/publications/apsnetfeatures/Pages/blackssigatoka.aspx.
Living on Earth, PRI's Environmental News Magazine, Top Banana, Air Date: Week of Apr. 18, 2014, 7 pages, P.O.Box 990007, Prudential Station, Boston, MA 02199 USA, Tel: 1-617-287-4121, email: comments@loe.org.
Spreadsheet, Pesticides Registered for Use in Banana in Hawai'i, Sep. 2, 2014, 3 pages, Label images provided by the Hawai'i Department of Agriculture Pesticides Branch.
Ebimieowei Etebu et al, Control of Black Sigatoka Disease: Challenges and Prospects, Department of Biological Sciences, Niger Delta University, Wilberforce Island, Bayelsa State, Nigeria, 7 pages, Accepted Jan. 12, 2011, auther email: eetebu@yahoo.com, Tel: +234-802-982-9015.
Gwynn Guilford, Quartz, The World's Favorite Fruit is Slowly But Surely Being Driven to Extinction, Nov. 30, 2015, 4 pages, http://qz.com/559579/.
Mark Koba, Yes! We Have No Bananas? It Could Actually Happen, 3 pages, Apr. 21, 2014, Mark Koba | @MarkKobaCNBC, http://www.cnbc.com/2014/21/.
Mark Koba, Fungus Threatens Banana Supply, 3 pages, Business Apr. 21, 2014, http://www.nbcnews.com/business/consumer/.
Nadia Ordonez et al, Worse Comes to Worst: Bananas and Panama Disease—When Plant and Pathogen Clones Meet, 7 pages, Published Nov. 19, 2015, http://journals.plos.org/plospathogens.
Jocanima Corporation, providing total agricultural solutions for maximum productivity, Fungicides, 4 pages, http://ocanima.com/product-lines/fungicides/.
DuPont Kocide Blue Xtra with BioActive Copper; "It's just the best copper fungicide around"; DuPont (Australia) Ltd., 168 Walker Street, North Sydney, NSW 2060, ABN 59 000 718 469, DuPont Product Hotline: 1-800-257-169; www.au.ag.dupont.com; 6 pages.
Encyclopaedia Britannica, Complex in Chemistry; http://www.britannica.com/EBchecked/topic/129940/complex; 2 pages.
E. Malka; I.Perelshtein; A. Lipovsky; Y. Shalom; L. Naparstek; N. Perkas; T. Patick; R. Lubart; Y. Nitzan; E. Banin and A. Gedanken; Eradication of Multi-Drug Resistant Bacteria by a Novel Zn-doped CuO Nanocomposite; Small Journal; wileyonlinelibrary.com; 2013; 8 pages.
Brian Blenkowski and Environmental Health News; Fish Cannot Smell in Polluted Waters; Scientific American, Mar. 18, 2013; http://www.scientificamerican.com/article/fish-cannot-smell-in-polluted-waters/; 3 pages.

(56) References Cited

OTHER PUBLICATIONS

Jim Graham, Novel Bactericides and Application Methods to Control Huanglongbing Disease of Citrus; University of Florida, Citrus Research and Education Center, Lake Alfred, FL 33850 USA; 5 pages.
Jost Chemical—It's in the Details; What is a Chelate? www.jostchemical.com; USA 1-314-428-4300; Europe +32 (0)85 231711; 2 pages.
DuPont Kocide 3000 Fungicide/Bactericide; http://www2.dupont.com/Prod_Agriculture/en-us/content/crop-protection/kocide-3000.html; 3 pages.
Y.A. Lee, M.N. Schroth, M. Hendson, S.E Lindow, X-L Wang, of Dept. of Plant Pathology, University of California, Berkely, 94720; B. Olson, R.P. Buchner of Cooperative Extension, University of California, Butte County and Tehama County, respectively; and B. Teviotdale of Kearney Agriculture Center, Parlier, CA 93648; (Present address of Y.A. Lee Dept. of Biology, Fu Jen University, HsinChuang, Taipei, Taiwan, Republic of China; Accepted for publication Sep. 13, 1993; The American Phytopathological Society 1993; 6 pages.
Material Fact Sheet Copper Products; Organic Resource Guide p. 89; www.cefs.ncsu.edu/newsevents/.../product 06-copperproduct.pdf; Center for Environmental Farming Systems; 7 pages.
Material Safety Data Sheet; NORDOX 30/30 WG, EPA Reg. No. 48142-7; manufactured by NORDOX as c/o Monterey AgResources, P O Box 350000, Fresno, CA 93745-5000; 559-499-2100 days; 559-994-9144 evenings; issued May 2007; 4 pages.
ADJUVANTS Product Guide—Nufarm; www.nufarm.com.au; 21 pages.
Specimen Label; Champ WG Agricultural Fungicide, EPA Reg. No. 55146-1; manufactured for Nufarm Americas Inc, AGT Division, 150 Harvester Drive, Burr Ridge, IL 60527, 2 pages.
Nufarm Agriculture Division; The Copper Champs! Unique Copper Hydroxide Formulations; Nufarm Americas Inc. 1333 Burr Ridge Parkway, Suite 125A, Burr Ridge, IL 60527-0866; 708-754-3330 (phone); 708-754-0314 (Fax); E-mail: www.nufarm.com; 12 pages.
Nufarm Tri-Base Blue Liquid Copper Fungicide; Nufarm State Office: WA (08) 9411 4000,. SA (08 8444 6300, VIC (03) 9282 1000 TAS (03) 6391 1966, QLD (07) 3893 8777, NSW (02) 6884 8180; www.nufarm.com.au; 8 pages.
Sandra Hardy, NSW DPI, Gosford Horticultural Institute; Keith Fallow, Nipro; Patricia Barkley, NSW DPI; Using Copper Sprays to Control Diseases in Citrus; NSW Dept. of Primary Industries; Nov. 2007, Primefact 757; 5 pages.
Paul Rusnak [Google+] 1; All Hands on Deck to Save Florida Citrus; http://www.growingproduce.com/citrus/insect-disease-update/all-hands-on-deck-to-save-fl . . . ; Feb. 2, 2015; 5 pages.
Tom Burfield; The Grower—Production Strategies for Commercial Growers; Search Continues for Copper Alternatives to Control Citrus Canker; Jan. 1, 2012; http://www.thegrower.com/issues/citrus-vegetable/136032403.html; 1 page.
Wikipedia, the free encyclopedia; Environmental Impact of Pesticides; modified Dec. 10, 2014; http://en.wikipedia.org/wiki/Environmental_impact_of_pesticides; 12 pages.
Wikipedia, the free encyclopedia; Pesticide; http://en.wikipedia.org/wiki/Pesticide; 10 pages.
M. Eshed, J. Lellouche, A. Gedanken and E. Banin; Advanced Functional Materials; A Zn-Doped CuO Nanocomposite Shows Enhanced Antibiofilm and Antibacterial Activities Against *Streptococcus* mutans Compared to Nanosized CuO; www.afm-joumal.de; 2014; Materials Views, www.MaterialsViews.com; 10 pages.
J. Graham, M. Dewdney UF/CREC; H.Yonce Kac Agricultural, Inc.; Comparison of Copper Formulations for Control of Canker on Hamlin Oranges; University of Florida IFAS Citrus Research and Education Center; 25 pages.
Copper Ferrite CuFe2O4, CAS 12018-79-0; American Elements; http://www.americanelements.com/cuferr.html; 2 pages.
Price Quote No. 150402RP07 to Robert Sabin dated Apr. 2, 2015; Copper Zinc Iron Oxide Nanopowder; PN: CUZN-FEO-0185M-NP.100N; Formula CuZnFe2O4; American Elements, Merelex Corporation, 10884 Weyburn Avenue, Los Angeles, CA 90024, 310-208-0551 (tele), 310-208-0351 (Fax); E-mail: orders@americanelements.com; 1 page.
Price Quote No. 150416RP03 to Robert Sabin dated Apr. 16, 2015; Zinc Iron Oxide Nanopowder; PN: Zn-FEO-02-NP.100N; Formula ZnFe2O4; American Elements, Merelex Corporation, 10884 Weyburn Avenue, Los Angeles, CA 90024, 310-208-0551 (tele), 310-208-0351 (Fax); E-mail: orders@americanelements.com; 1 page.
Written by: Editors of Encyclopaedia Britannica: Ferrite—Iron Oxide Compound; http://www.britannica.com/EBchecked/topic/205072/ferrite; 1 page.
Sigma-Aldrich Copper Iron Oxide CuFe2O4; http://www.sigmaaldrich.com/catalog/product/aldrich/641723?lang=en&region=US; 2 pages.
Sigma-Aldrich Copper Zinc Iron Oxide CuZnFe2O4; http://www.sigmaaldrich.com/catalog/product/aldrich/641650?lang=en&region=US; 2 pages.
Sigma-Aldrich Order Confirmation No. 3013972345 to Superflox Therputics, PO Box 332, Mill Neck, NY 11765 USA dated Apr. 6, 2015; Sigma-Aldrich Inc., 3050 Spruce Street. St. Louis, MO 63103 US; www.sigmaaldrich.com/help-welcome/ordering-product/terms-and-conditions-of-sale.html; 1 page.
Sigma-Aldrich Technical Service Answer Scientist's Response Via Email (Jeanne Harrell) to Robert Sabin, re: 641650: Copper Zinc Iron Oxide dated Apr. 14, 2015; 1 page.
Wikipedia, the free encyclopedia—Ferrite (magnet): http://en.wikipedia.org/wiki/Ferrite_(magnet); 5 pages.

\* cited by examiner

X-Ray Diffraction

Shows that the particles are $Cu(OH)_2$ with no iron oxide or hydroxide peak, indicating that the $Cu(OH)_2$ is doped with iron.

Elemental Analysis

Shows the presence
of both iron and copper

Quantitative results

POTENTIATION OF FIXED COPPERS AND OTHER PESTICIDES CONTAINING COPPER AND SUPPLEMENTING PLANT NUTRITION

RELATED APPLICATIONS

This application is a continuation in part of application Ser. No. 14/689,675, filed Apr. 17, 2015, which '675 application is a continuation-in-part of application Ser. No. 14/674,607 filed Mar. 31, 2015, which '607 application is a continuation-in-part of application Ser. No. 14/625,405, filed Feb. 18, 2015, which applications are incorporated by reference herein and claims benefit therefrom under 35 U.S.C. 120. This application and the aforementioned '405 application are based upon, and claim priority under 35 U.S.C. 119(e) from, provisional application Ser. No. 62/002,330 filed May 23, 2014, 62/003,528 filed May 27, 2014, 62/020,247 filed Jul. 2, 2014, 62/021,819 filed Jul. 8, 2014 and 62/094,775 filed Dec. 19, 2014. These applications are incorporated by reference herein.

FIELD OF THE INVENTION

The present invention relates to potentiation of pesticides containing fixed copper in human, agricultural, fungicidal, bactericidal, anti-pathogen and biocidal applications, by increasing the activity of its biocidal effects, so that less polluting copper is used.

BACKGROUND

All Patents, scientific articles and other documents mentioned herein are incorporated by reference as if reproduced in full.

During the 2015 Florida Citrus Show in Fort Pierce, Fla., a 2-day conference, genuine desperation is clearly seen because it is disclosed that most of Florida is infected with Huang-longbing (HLB) bacteria and there are no good treatments for this devastating disease which will all but destroy the Florida citrus industry. See also, Rusnak, "*All Hands On Deck to Save Florida Citrus*", 2015, http://www.growingproduce.com/citrus/insect-disease-update/all-hands-on-deck-to-save-florida-citrus/. Growers were almost crying as they are abandoning their groves, selling their land, pleading with scientists to do something, anything, a stop gap measure. At the scientific presentation, the scientists were at a loss to offer anything substantial at this time. Vague promises were made 5 years down the line, etc., that they may have something to counter HLB. Virtually all the growers are hanging on by their fingernails. Moreover, the mirror image of the situation in Florida is being played out in Italy where a similar systemic bacteria is killing centuries old olive trees. The natural course of both diseases is very similar, inescapably progressing to death, and again there are no good treatments. Unless a solution is found within 7 years, there will be little citrus or olive trees in Florida or Italy, respectively. Moreover, with global warming and climate change there will be many plant pests, insects, bacteria, and fungi extending their range moving into new territory severely impacting the way of life and the food supply of millions.

An example is the devastating Xylellafastidosa infection of olive trees, in Italy, discussed in "*XylellaFastidosa: It's Biology, Diagnosis, Control, And Risks*" by J. D. Janse and A. Obradovic. This infection is almost a mirror image of HLB infection of citrus. Xylella infection is a bacterium, which inhabits the internal vascular compartment of the olive tree, the xylem, and causes like HLB, plants to dry out, die, leaving shriveled stumps, that are incapable of bearing fruit. See also the Daily Mail, in the published article at "*Olive Oil Under Threat From Bacteria Which Is Hitting Hundreds Of Thousands Of Trees In Italy—And Could Set Prices Soaring*" by Hannah Roberts, and "*Italian Government Urged To Take Action To Fight Against Olive Tree Epidemic*" in Agro News, Jan. 9, 2015. Like HLB, there are few treatments which target the internal vascular system of olive trees.

HLB disease of citrus is a devastating phloem limited incurable bacterial infection which is decimating/killing the citrus industry worldwide. See, "*Novel Bactericides and Application Methods to Control Huanglongbing Disease of Citrus*" which discusses an overview of "inconsequential effect of nutritional treatments on Huanglongbing control, fruit quality, bacterial titer and disease progress" by T. R. Gottwald, J. H, Graham, et al. See also, "*Citrus Disease with No Cure is Ravaging Florida Groves*" Lizette Alvarez, New York Times, which provides: "We just need somebody to figure out how we can kill this bacteria in these trees." See also, "*Citrus Greening Forces Florida Growers To Trust A Controversial Savior*" Huffington Post 2013/08/30, which discloses that most commercial growers have adopted foliar nutrition as a stop gap method to fend off the inevitable dying of their citrus trees. See also, "*Overview of Citrus Grower Nutritional Spray Compositions*" Tim Spann, which discloses "every fertilizer manufacturer now produces their own program of foliar nutrition for HLB." Further disclosed is the "Maury Boyd cocktail", which is the original nutritional foliar spray for HLB disease support.

Copper (II) hydroxide, also known as cupric hydroxide and having the chemical formula $Cu(OH)_2$, has a wide variety of commercially important uses, including as a mordant and pigment in dyeing textile and paper fibers, in the preparation of catalysts and other copper compounds, in marine paints, and in fungicides and bactericides. There are tens of millions of pounds of copper hydroxide pesticides, fungicides, bactericides, and biocides used throughout the world yearly, including about three million pounds a year in California alone. The Material Fact Sheet for "*Copper Products*" in the Organic Resource Guide from the Center for Environmental Farming Systems, www.cefs.ncsu.edu/newsevents/ . . . product06-copperproducts.pdf discloses at page 93 that copper is labeled for use on over 100 crop plants to control fungal and bacterial diseases. Page 94 discloses a chart labeled "*Copper Studies Showing Fair or Good Efficacy.*"

As noted in PCT Patent Publication WO 2006028853 A1 of Oberholzer, Method for stabilizing copper hydroxide, Publication date Mar. 16, 2006, the patent literature discloses a variety of processes for the commercial manufacture of copper (II) hydroxide. U.S. Pat. Nos. 2,924,505, 3,428,731, 3,628,920, and RE 24,324 disclose processes involving phosphate. U.S. Pat. Nos. 4,490,337 and 4,808,406 disclose processes involving carbonate; the latter process provides a product comprising considerable copper carbonate, in addition to copper hydroxide. U.S. Pat. Nos. 1,800,828, 1,867,357, 2,525,242, 2,536,096 and 3,635,668 disclose processes involving ammonia. The processes of U.S. Pat. Nos. 2,525,242 and 2,536,096 involve oxidation of copper metal in the presence of ammonia and U.S. Pat. No. 4,944,935 discloses a similar process substituting ammonium ion for all or part of the ammonia. The other processes start with a soluble copper salt, typically copper (II) sulfate. U.S. Pat. No. 4,404,169, European Patent Number EP 80226 B1 and PCT Patent Publication WO 02/083566 A2 describe processes starting with copper (II) oxychloride. J. Komorowski-Kulik, Zeszyty, Naukowe Politecniki Sitaskiej, Series: Chemistry 2001, 142, 59-66 discloses a process where an aqueous suspension of copper (II) oxychloride is contacted with aqueous sodium hydroxide in the presence of glycerol as stabilizer, (See PCT Patent Publication WO 2006028853 A1 of Oberholzer, Method for stabilizing copper hydroxide, Publication date Mar. 16, 2006). Oberholzer, in U.S. Pat. No. 7,402,296, claims priority from the aforementioned PCT Patent Publication WO 2006028853 A1 of Oberholzer.

Nufarm discloses the history of copper fungicides, the history of copper hydroxide, how copper hydroxide works, how copper works, particle size of copper hydroxide fungicide and more information, including about their products Champ® Dry Prill, Champ® Formula 2 Flowable and Champion® WP (See Nufarm Americas Inc., Nufarm Agriculture Division, "*The Copper Champs!*" ©2002.)

DuPont discloses a similar product, DuPont Kocide Blue Xtra with similar information. (DuPont (Australia) Ltd., DuPont™ Kocide Blue Xtra with BioActive Copper® ©2006) DuPont discloses a bewildering array of dozens of plant diseases, treated with DuPont™ Kocide® 3000 Fungicide/Bactericide, on a multitude of agricultural crops. (E.I. DuPont de Nemours & Company Crop Protection, DuPont™ Kocide® 3000 Fungicide/Bactericide, ©2006-2011.)

Copper pesticides, fungicides, and bactericides are extremely toxic to fish and aquatic organisms. (Nufarm Americas Inc., Agt Division, Champ® WG Specimen Label). Runoff from the use of copper fungicides, bactericides and algaecides into waterways, ground water and the ground is a very serious contamination problem well known to those in the art. For example, Scientific American, Mar. 18, 2013, "*Fish Cannot Smell In Polluted Waters*" by Brian Bienkowski, discloses: "copper is a poster child for water pollution" said Nathaniel Scholz, an excitology program manager at the National Oceanic and Atmospheric Administration's (NOAA) Northwest Fisheries Science Center, further noting "copper is intensively used as a pesticide, fungicide . . . it's found in cars, in boat paint, so boatyards are often contaminated, and it's often found in industrial discharge and near legacy mining operations. It's a rare pollutant that's both agricultural and urban." Young coho salmon exposed to low levels of copper did not evade predators—cutthroat trout—nearly as well as unexposed salmon, according to a lab study by Scholz and colleagues. The problem is "likely to be widespread in many freshwater aquatic habitats" according to a NOAA report. Copper at low concentrations targets the neurons that help fish avoid predators, but at higher concentrations, copper impairs their smell for everything.

The Alabama State Water Program, of the Alabama Water Quality Information System—FAQ results, discloses that agricultural pesticides are considered a potential source of copper pollution for water, and that 10 million pounds of copper was used in agricultural fungicides in the U.S. alone in 1990, "much of the copper is sprayed on plants and tends to accumulate in the immediate soil environment, making it susceptible to storm water runoff from agricultural operations."

"*The Grower*", Jan. 1, 2012 by Tom Burfield, discloses that "now, producers are growing increasingly anxious about the effect copper buildup may have on their groves, and they're increasingly afraid that the day will come when pathogens display copper resistance."

U.S. Pat. No. 5,202,353 of Schroth, Iron Enhancement of Copper Based Fungicidal and Bactericidal and Bactericidal Compositions, 1993, discloses that the addition of soluble iron to copper hydroxide fungicide increases activity of the copper hydroxide fungicide bactericide and reverses resistance to copper in vitro. Also, U.S. Pat. No. 5,385,934 of Schroth, Methods for Preventing Precipitation of Copper Based Bactericidal Compositions Containing Iron, 1995, discloses the addition of an aggregation inhibiting salt to the copper plus iron compositions to prevent aggregate/or sediment formation upon the addition of Fe+3 to the composition. Both of Schroth's patents taken together require five components—a copper hydroxide component or a fixed copper component, with a dry surfactant, plus a soluble iron component, plus a liquid surfactant, and plus an aggregation inhibitor, salt. Without being limited, held or bound to any particular theory or mechanism of action Applicant believes that because the copper component and the iron components are separate, the copper hydroxide being insoluble, the iron components being both soluble and insoluble, the aggregation inhibitor, the dry surfactant, and the liquid surfactant, the sizes being vastly different, then it follows that the release rate and quantities and bioavailability of copper and iron ions on plant surfaces is not identical, or regulated, so that each component may release and disperse their ions at different rates compromising the pesticidal, fungicidal, bactericidal and biocidal effects of the composition. Moreover, it is complicated to have 5 different separate components, with different solubilities; namely a copper component, iron components, two different surfactants, and the aggregation inhibiting component. Schroth's iron component is soluble, so that when sprayed on plant leaves, would tend to disappear in the rain, and thus be of little value. This compelled Schroth to disclose, for example, page 1463, in the sentences before discussion, of Lee and Schroth's paper, "in these experiments, insoluble ferric oxide was used to replace half of the concentrations of ferric chloride for the purpose of increasing persistence." See Lee, Schroth, et al., "*Increased Toxicity of Iron-Amended Copper-Containing Bactericides to the Walnut Blight Pathogen Xanthomonascampestrispv.juglandis*" Phytopathology, Ecology ad Epidemiology, The American Phytopathological Society, 1993, pgs. 1460-1465 (referred to herein as "*Schroth/Lee*"). Phytotoxicity was noted on trees treated with Champion® plus both ferric chloride and ferric oxide, although there was no difference in the efficacy between these two treatments. Page 1464 of Schroth/Lee discloses: "the effect of copper-iron mixtures in reducing blight of nuts has not been significantly better then copper compounds alone to date" and "whereas copper compounds are very effective in controlling blight of leaves, they have never demonstrated such effectiveness on nuts." Schroth/Lee also concludes on page 1464, "although the addition of ferric chloride to fixed copper compounds increases the concentration of free copper ions, phytotoxicity has not been observed in the field. However, phytotoxicity occurred when the insoluble ferric oxide was combined with ferric chloride. The reasons for this are unknown but probably have something to do with the long-term release of iron ions that interact with the fixed coppers. This surprising result indicates that much work yet has to be done to find the best formulation that will result in the greatest kill of bacteria over an extended period of time while at the same time not harming tender walnut tissues."

"The effect of iron in increasing the efficacy of copper compounds offers a new advance in the use of the age-old copper compounds and should lead to greatly improved control of bacteria such as X.c.juglandis. However, this will greatly depend on both the ecology of copper-resistant bacteria and the efficacy of new formulations in eradicating established populations."

Schroth's/Lee's paper, and Schroth's patents are clearly not enabling for "new formulations," taken together with the failure of "persistence" with their soluble irons on plant leaves, and unacceptable phytotoxicity. When Schroth/Lee tried to ameliorate the lack of persistence with the addition of insoluble iron to their soluble iron, their paper in the author's own words discloses their invention is unworkable. Their call for "new formulations" says it all, as well as their statement "much work yet has to be done." Schroth's disclosures have never caught on in commerce because of the complicated nature of their practice and problems with the release of ions, phytotoxicity, persistence, lack of activity, rain fastness and unperfected development.

Jim Graham, Megan Dewdney, in "*Comparison of Copper Formulations for Control of Canker on Hamlin Oranges*" disclose the testing of 14 different dosages of 11 distinct copper formulations. The formulations range from insoluble copper compounds, complexes, chelates to soluble copper chelates. No copper treatment was very effective on fruit incidents at harvest. A preferred size for systemic uptake according to Graham is 5 to 10 nm. See Graham, Jim, *Novel Bactericides and Application Methods to Control Disease of Citrus*, IV International Symposium of Plant-Pathogenic Bacteria, Guadalajara, Jalisco, Mexico, Sep. 23, 2014, University of Florida, UF-IFAS, especially third page from end, entitled *Alternative bactericide must be non phytotoxic and systemic. i.e., capable of loading into the phloem via foliar application.* No insoluble coppers tested by Graham had a particle size of 5-10 nanometers, so that none of the compounds of Graham's testing are capable of systemic administration to the plant through the stomata.

Zinc-doped CuO nanocomposites of a specific size are known for use in specific fields. Eyal Malka et al., (small 2013, DOI:10.1002/sm11.201301081, www.small-journal.com) discloses, "eradication of multi-drug resistant bacteria by a novel zinc-doped CuO nanocomposite." Michal Eshed, et al., (*Advanced Functional Materials* 2014, pp. 1382-1390, www.afm-journal.de) discloses, "a Zn-doped CuO nanocomposite shows enhanced anti-biofilm and antibacterial activities against Streptococcus mutans compared to nanosized CuO." They conclude, "the results of the present study further highlight the potential of these novel Zn:CuO np's as inhibitors of biofilm within the context of the oral niche." Moreover, Richardson provides, "commercially produced cupric oxide (copper(2) oxide) is ineffective as a fungicide or bactericide due to small surface areas; that is, dissolution times are very long compared to other basic copper (2) compounds," see H. Wayne Richardson in the "*Handbook Of Copper Compounds And Applications*" pg. 109. This CuO used by Malka and Eshed is the same copper referred by Richardson above. While 30 nm sized Zn:CuO nanocomponents are known, Applicant submits that taken together, biofilm in the oral niche and coatings of linens and antimicrobial bandages, they do not relate in any way to agricultural pesticide, and systemic plant protectorants. Moreover the size of 30 nm previously disclosed does not conform to Graham's teaching of 5-10 nm for systemic administration to citrus plants.

Ploss, et al, U.S. Pat. No. 7,105,136 B2, discloses that doping 5 wt % zinc metal into a copper salt composition intended for agricultural applications provided enhanced surface adhesion, as in the case of plants on leaf and fruit surfaces, thereby increasing the duration of the plant-protecting effects and also eliminating the expense and environmental emissions associated with the re-application of prior art compositions that would be required to provide the same level of protection. Ploss's use of metallic zinc to provide enhanced surface adhesion does not teach any advantages with regard to pesticidal characteristics per se. For example, zinc is a metal, an element and is insoluble in water, with a small surface area. Floss provides no teaching or suggestion that its metallic zinc is pesticidal as "enhanced surface adhesion" is clearly taught. This is known to those of knowledge of the art as an "adjuvant." Exemplary examples of the overwhelming plethora of agricultural adjuvants are: Nufarm, "*Adjuvants Product Guide*" pg 16, and Momentive, Momentive Adjuvants, Silwet and Agrospread adjuvants. Nufann's Spraymate bond is a high quality sticker, deposition and retention agent for use with contact or protectant type fungicides or with contact and ingested insecticides. Spraymate bond increases adherence of spray droplets by sticking them finnly to target surfaces. This protects pesticides against wash-off by rain or sprinkler irrigation. Spraymate bond also protects chemicals by slowing the rate of degradation immediately after application. Its key benefits are that it improves spray droplet deposition, retains and protects droplets on targets, improves the performance and life of protectant fungicides and contact insecticides. Furthermore, there is a world of difference between pure zinc metal, an element, and insoluble pesticidal zinc compounds.

SUMMARY OF THE INVENTION

This invention is directed to a pesticide, fungicidal, bactericidal, anti-pathogen or biocidal composition including a) at least one biologically inert carrier and; b) at least one doped component comprising at least one fixed copper compound, such as copper hydroxide, doped with at least one compound selected from the group consisting of iron compounds, zinc compounds, magnesium compounds, calcium compounds, and combinations thereof. In a preferred embodiment, the doped component only includes iron compounds and/or zinc compounds as the only doping compounds. Preferably, the doped component has a particle size of about 0.5 nm to 30 microns. The iron compound and/or zinc compound are doped into the fixed copper compound, such as copper hydroxide, singly or together in combination. In one embodiment a fixed copper compound is doped with an insoluble iron compound, such as, for example, where the fixed copper compound is copper hydroxide, and wherein the fixed copper compound is partially substituted by an insoluble iron compound. Optionally, a surfactant may be included in the composition to provide for a more efficacious formulation.

One advantage of Applicant's invention is that the composition includes doped components that contain both the fixed copper compounds and the iron, zinc, magnesium, and/or calcium compounds combined on the doped component. The fixed copper compound, such as copper hydroxide, doped with the iron compound and/or zinc compound is used in order to provide a more cost effective composition with increased activity as compared to copper hydroxide alone. Therefore, less copper is required with its resultant reduced runoff, and less pollution derived from copper. Moreover, iron is a plant micronutrient and the present composition would supply iron to plants as against copper hydroxide alone. It has been found that heavy use of copper compounds produces iron chlorosis. In addition, copper hydroxide is a pesticide, fungicide/bactericide that is so well established so that the present invention could be administered very similarly to the current methods of copper hydroxide administration with a straight substitution, more or less, except that the amount of elemental copper derived from the present invention will be reduced, as against stand-alone copper hydroxide, to achieve the same or greater control or pathogen reduction. In one embodiment of the present invention, Applicant submits that the present invention may be substituted for the copper hydroxide in PCT Patent Publication WO 2006028853 to Oberholzer. The composition of the present invention also reverses resistance to copper so that copper resistant pathogens become sensitive to copper.

While the Material Data Sheet for Copper Products, page 94, discloses a list of crops with poor results with copper, it is believed that Applicant's present invention increases the activity of copper with respect thereto. In one embodiment, Applicant's present invention may be provided as a pesticide, fungicide, bactericide, anti-pathogen and biocidal nutrient spray with optional additional micronutrients and/or optionally macronutrients, so that there would be a combination copper based pesticide with micronutrients all in one formulation. In another embodiment, Applicant's present invention includes an insoluble copper pesticide, fungicide, bactericide, and anti-pathogen and biocidal capable of systemic uptake by foliar, root and/or trunk injection, and a plant protectorant, dual mode of action, all in one compound.

The prior art teaches various complexes of copper compounds, mixtures which are two or more substances that are not chemically combined, and chelates of copper compounds. Compounds of the present invention are overwhelmingly, compellingly, and persuasively, distinguishable, as doped zinc compounds and doped iron compounds are internalized in the copper hydroxide or other fixed coppers. Complexes and chelates are joined so that they are externalized to the copper hydroxide or other fixed coppers. Moreover, being externalized to the copper hydroxide or other fixed copper produces larger particulates undesirable for systemic administration.

Applicant's doped components can also be sized at about 5 nm-10 nm, and other larger particulates, in one embodiment, to provide both plant protectorant and systemic uptake to be carried internally through the plant phloem and xylem to kill systemic bacterial infections such as HLB, and Xylellafastidosa, and other systemic pathogenic fungi, or internal pathogens. Applicant's doped composition of fixed coppers doped with zinc, iron, or both, are also useful in treating banana plants afflicted with Black Sigatoka disease, Yellow Sigatoka disease and Panama disease.

The Applicant's invention clearly will not displace and replace the entire world use of pesticides. However, applicant's invention will clearly replace and displace many of the highly toxic pesticides currently being used against pests which are resistant to existing copper pesticides.

Moreover the Applicant's invention will decrease the breadth, depth and range of pesticides currently resistant to copper pesticides, restoring sensitivity and high activity. Moreover a Google search discloses over 52 million hits for the well-known established harmful effects of pesticides.

Moreover, Wikipedia discloses, "*Environmental Impact of Pesticides*" with one page and a half of horrific pesticide enviromnental effects of classes of pesticides. In contrast, the Applicant's present invention reduces the need for the quantity of copper currently being used as a pesticide and displaces and replace many current highly toxic poisonous pesticides currently being used. Copper is the lesser of the two evils as against synthetic agricultural chemical pesticides with their well-known toxicities and horrific environmental effects.

BRIEF DESCRIPTION OF THE DRAWINGS

The preferred embodiment of the present invention can best be understood in connection with the accompanying drawing. It is noted that the invention is not limited to the precise embodiments shown in drawings, in which.

DETAILED DESCRIPTION OF THE INVENTION

Figure 1:
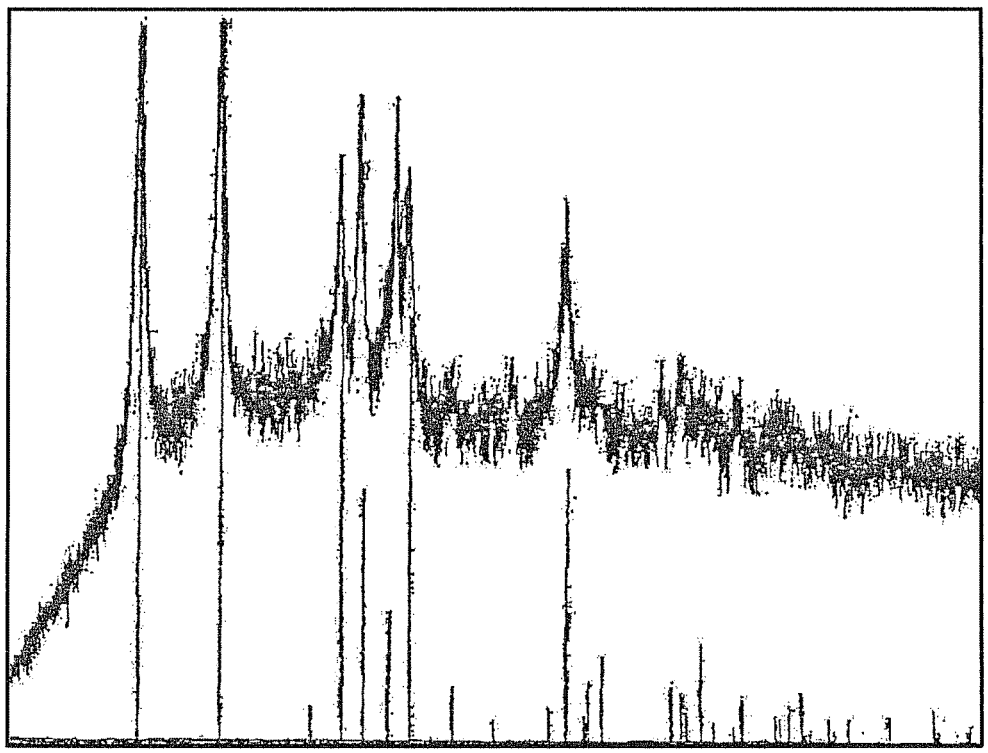
FIG. 1 is a copy of an X-Ray Diffraction test showing copper hydroxide doped with 15 at % insoluble iron as a dopant in accordance with one embodiment of the present invention. There are no additional peaks proving that the iron is incorporated within the copper hydroxide.

The invention is a pesticide, fungicidal, bactericidal, anti-pathogen or biocidal composition comprising a) at least one biologically inert carrier; and b) at least one doped component including at least one fixed copper compound doped with at least one compound selected from the group consisting of iron compounds, zinc compounds, magnesium compounds, calcium compounds and combinations thereof. In a preferred embodiment, the doped component only includes iron compounds and/or zinc compounds as the only doping compound. For example, copper hydroxide may be doped with iron hydroxide, iron oxyhydroxide or other iron compound as one doped component. In one embodiment, the fixed copper compound is doped with an insoluble iron compound, wherein the fixed copper compound is partially substituted by the insoluble iron compound. The invention also comprises a fixed copper compound, such as copper hydroxide, doped with a zinc compound. Furthermore, the fixed copper compound, such as copper hydroxide, may be doped with both an iron compound and a zinc compound. Applicant's invention includes at least one doped component containing both the fixed copper compound doped with an iron compound and/or a zinc compound that can be used similarly to how copper hydroxide alone is used. In one embodiment of the present invention, an iron compound is doped on copper hydroxide, a zinc compound is doped on copper hydroxide, a zinc compound and an iron compound are doped on copper hydroxide, singly and optionally combined together, and or added to other pesticide agents. The doped component is prepared according to methods described herein and readily understood to those of skill in the art. The composition can be used in many of the applications that copper hydroxide is currently utilized, and many new pesticidal indications which are currently resistant to copper. See, for example, WO2006028853. In a preferred embodiment, copper hydroxide is doped with iron hydroxide to provide 15 at % iron to the doped component, which results in a black doped component. In another preferred embodiment, the atomic percentage (at %) of iron in the doped component is less than 15 at %, more preferably less than 10 at %. Because of the increased biocidal activity, the preferred copper hydroxide-iron hydroxide doped component prepared by the present method is especially useful as an active ingredient in pesticides, fungicides, bactericides and biocides. This increased biocidal activity reduces the number of pathogens currently resistant to copper pesticides, increasing the range and breath of activity of copper against other bacteria, fungi, viruses, mycoplasma, and other pathogenic organisms.

Preferably, the composition is administered to plants by a method selected from the group consisting of dusting, sprinkling, spraying, brushing, dipping, smearing, impregnating, injection of the composition into plant vasculature, and application to a root system.

DEFINITIONS

In the context of this application, several terms are utilized as follows:

The definition of "pesticide" used in this application refers to the United States EPA definition page 1 of www.epa.gov/agriculture/tpes.html which is "A pesticide is any substance or mixture of substances intended for preventing, destroying, repelling, or mitigating any pest. Pests can be insects and insect-like organisms, mice and other vertebrate animals, unwanted plants (weeds), or fungi, bacteria and viruses that cause plant diseases. Though often misunderstood to refer only to insecticides, the term pesticide also applies to herbicides, fungicides, and various other substances used to control pests."

The definition of a "mixture": a mixture contains 2 or more substances that are not chemically combined. Mixtures are unlike chemical compounds, because: the substances in a mixture can be separated using physical methods such as filtration and distillation. Mixtures have variable compositions while compounds have a fixed definite formula. When mixed, individual substances keep their properties in a mixture, while if they form a compound their properties can change. See http://www.chemicool.com/definition/mixture.html). An example of a mixture is NORDOX 30/30 wg, manufactured by NORDOX AS c/o Monterey AgResources, EPA Reg. No. 48142-7), which is a cuprous oxide and zinc oxide mixture.

The definition of "elements" and "compounds": "Elements and compounds are pure chemical substances found in nature. The difference between an element and a compound is that an element is a substance made of the same type of atoms, whereas a compound is made of different elements in definite proportions. Examples of elements include iron, copper, zinc, hydrogen and oxygen. Examples of compounds include water ($H_2O$) and salt (sodium chloride-NaCl)." See, http://www.diffen.com/difference/Compound_vs_Element.

The definition of "complex": "A complex is a molecular entity formed by loose association involving two or more component molecular entities (ionic or uncharged), or the corresponding chemical species. The bonding between the components is normally weaker than in a covalent bond. In inorganic chemistry the term "coordination entity" is recommended instead of "complex" (IUPAC inorganic NOMENCLATURE (1990))." See, http://www.chemicool.com/definition/complex.html.

The definition of "chelate": "In reality, a chelate is any metal that is attached to an anion (negatively charged group) with more than one attachment site. Chelation means that the anion has two or more separate sites to which the metal is bonded." See, www.jostchemical.corn.

The definition of a "dopant": a dopant is "an impurity added usually in minute amounts to a pure substance to alter its properties." See, www.merriam-webster.com/dictionary/dopant. According to www.freedictionary.com, under "medical" the term "to dope" is used in materials sciences as a verb which means "To add or incorporate a substance or other additive to a chemical compound of interest, with the intent of improving or altering performance parameters."

The definition of "fixed copper": a copper compound which is insoluble or highly insoluble in water. Fixed Coppers are further disclosed by H. Wayne Richardson in the "*Handbook Of Copper Compounds And Applications*", page 97 third paragraph, "suitable copper compounds include fixed coppers [Cu+(OH)2], Bordeaux, as well as other well known fixed copper compositions including those disclosed in CRV Handbook of Pest Management in Agriculture, Vol. 3, David Pimentel (editor), CRC Press, Boca Raton, Fla. (1981), which is incorporated herein by reference" and Sabin '196 patent such as copper oxide/cuprous oxide, copper oxychloride, tribasic copper sulfate ($CuSO_4$ $3Cu(OH)_2$, copper diammonia diacetate complex and/or any other well-known fixed or insoluble copper compositions currently being used, or has been prior used as a pesticide, fungicide, bactericide, and algaecide. Exemplary examples are copper hydroxide, copper/cuprous oxide, copper carbonate, copper oxychloride, basic carbonate, copper carbonate, basic copper sulfates including particularly tribasic copper sulfate, copper oxychlorides, and mixtures thereof, ammonia copper carbonate, basic copper chloride, and others, and mixtures thereof.

The term "iron doped copper hydroxide" refers to a copper hydroxide compound that is doped with an iron compound. It is understood in alternate embodiments that the copper hydroxide compound may be substituted with another fixed copper compound as provided herein.

The term "zinc doped copper hydroxide" refers to a copper hydroxide compound that is doped with a zinc compound. It is understood in alternate embodiments that the copper hydroxide compound may be substituted with another fixed copper compound as provided herein.

The term "zinc and iron doped copper hydroxide" refers to a copper hydroxide compound that is doped with both an iron compound and a zinc compound. It is understood in alternate embodiments that the copper hydroxide compound may be substituted with another fixed copper compound as provided herein.

Examples of iron compounds include any insoluble or substantially insoluble iron compound. Further examples include, but are not limited to iron compounds selected from the group consisting of iron hydroxide, iron oxyhydroxide, iron oxide, iron glucose, ferric citrate, Ferritin, ferrous fumarate, and ferrous sulfate. Most preferably the iron compound is iron hydroxide and/or iron oxyhydroxide.

Examples of zinc compounds include any insoluble or substantially insoluble zinc compound. Further examples include, but are not limited to zinc compounds selected from the group consisting of zinc hydroxide and zinc oxide.

In a preferred embodiment, the term "insoluble or substantially insoluble" is used herein. However, based on industry standards, Applicant submits that there is not a hard and fast quantitative definition for such terms as used by those of skill in the art. Accordingly, terms such as "sparingly soluble", "insoluble", "highly insoluble", "slightly soluble", ("negligible") etc. have been used for decades by those of skill in the art. See, for Example U.S. Pat. No. 5,385,934, at column 1, lines 28-38, wherein Professor Emeritus Milton N. Schroth provides that "These copper based compositions are typically aqueous" fixed" copper based compositions because the copper compounds used in these compositions typically have a solubility of free $Cu+2$ from about 1 to 30 ppm in the aqueous solution with the remainder (and the vast majority) of the copper either being insoluble or in chelated form (i.e., "fixed"). The 1 to 30 ppm of $Cu+2$ in such aqueous compositions is typically referred to as "free copper" to distinguish it from either the chelated $Cu+2$ or the insoluble $Cu+2$ in these fixed copper compositions." Similarly, Professor Santra discloses in U.S. Pat. No. 8,221,791 B1 "An important consideration is whether to use "soluble" or "insoluble" copper(Cu) for long term fungicidal or bactericidal protection. The "soluble" Cu refers to Cu based salts (such as Cu sulphate) that hydrolyze completely in water, producing ionic Cu. The "insoluble (sparingly soluble) Cu compounds act as a reservoir from which Cu ion is released to the plant surface on which it is deposited upon application." Additionally, Professor Santra provides "Currently used Cu compounds possess unique set of physical and chemical properties. They differ in their total amount of metallic Cu content and aqueous solubility. It is well understood that the antibacterial activity will depend upon the availability of soluble (free and reactive) Cu ions in the formulation. Among the existing Cu compounds, tribasic Cu sulphates and cuprous oxide are least soluble, whereas Cu hydroxides are more soluble than Cu oxychloride." And Professor Santra further provides "Several Cu compounds are registered in the United States for management of over 100 diseases on almost 50 food crops. The Cu compounds exhibit varying degrees of effectiveness for any target organism on any given host. The most common forms of Cu that satisfy these conditions to varying degrees are the normal hydrolysis products of Cu(1) and Cu(2) salts (also known as "insoluble Cu" of "fixed Cu" compounds: Cu(1) oxide, ($Cu_2O$), Cu(2) oxychloride($CuCl_2 \cdot 3Cu(OH)_2$), tribasic Cu(2) sulphate($CuSO_4 3Cu(OH)_2$, and Cu hydroxide(Cu $(OH)_2$." In Agrochemical and Pesticide Safety Handbook, Michael F Waxman discloses "Since copper is toxic to plants, it must be used at low levels or in the insoluble form. For this reason, the relatively insoluble or "fixed" copper salts are used. These compounds release copper ions at very low rates that are adequate for fungicidal activity but not at concentrations that would harm or kill host plant." Richardson discloses "Alternate products were developed primarily in the twenties and thirties and relied on low soluble or fixed coppers which could be applied as dusts or suspensions" and "A copper compound must be chosen that is relatively resistant to weathering and supplies enough copper to be toxic to the fungal spores and bacterial cells without adversely affecting the host. The most common forms of copper that satisfy these conditions to varying degrees are the normal hydrolysis products of copper(1) and copper(2) salts: copper (1) oxide(Cu2), cuprous oxide), copper(2) oxychloride($CuCl_2 \cdot 3Cu(OH)_2$, tribasic copper(2)sulphate ($CuSO_4 \cdot 3Cu(OH)_2$, and copper hydroxides($Cu(OH)_2$). These "fixed coppers" offer advantages of application and reduced phytotoxicity over the classic Bordeaux mixture. "These are the terms Richardson uses: Pg 85, Copper(2) Phosphate Trihydrate, "insoluble in cold water", Pg 55, Copper(1) Oxide, "virtually insoluble in water" Copper(2) oxide, Pp. 57,58, "essentially insoluble in water", Pg 61, Copper(2)Hydroxide, "virtually insoluble in water", Pg 63, Copper(2) carbonate Hydroxide, "virtually insoluble in water", Pg 69, Copper(2) Oxychloride, "essentially insoluble in water", Pg 79, Basic Copper(2) sulphate, "insoluble in water", Pg 83, Copper(2)Gluconate, "soluble in water." Richardson discloses a multitude of Copper compounds and descriptive nomenclature describing their solubility as above demonstrated.

Those of the skill in the art can readily and easily test to determine the lower doses required of the applicant's invention to achieve disease control, and the doses to achieve disease control on copper resistant pathogens by standard routine testing.

The iron doping of the copper hydroxide nanoparticles is from a trace contamination of iron, less than 0.01 at %, to about 40 at % iron with about 5-15 at % elemental iron preferred, with about 15 at % elemental iron the most preferred quantity. Other fixed coppers may incorporate more than 40 at % iron and/or zinc. While a variety of processes may be used to manufacture the doped component of the present invention, Applicant has used a wet chemical process as further indicated in detail below. It is understood to those of skill in the art that the process disclosed herein is scalable for commercial production. The product is dried/ evaporated by methods well known to those skilled in the chemical art, and may be overcoated, if desired, with a stabilizer by methods well known to those in the chemical art. For example, See U.S. Pat. No. 4,404,169 to Ploss, et al. entitled *Process For Producing Cupric Hydroxide.* The preferred size of an iron doped copper hydroxide nanoparticle is sub-micron, from about 0.5 nm to 30 microns. A more preferred size is from about 3.5 nm to 15 microns, an additional preferred size is from about 3.5 nm to 200 nm. A most preferred size is from about 3.5 nm to 10 nm, especially for both leaf protectorant and systemic activity all in one. Different sizes may be mixed together in the practice of the invention.

Moreover, fixed copper compounds, such as copper hydroxide, are generally insoluble or highly insoluble in water. While not being limited, held or bound to any particular theory or mechanism of action, it is generally thought that "The free copper penetrates into the bacterial and/or fungal micro-organism in order to exert its toxic effect." (See U.S. Pat. No. 5,202,353 of Schroth, Iron Enhancement of Copper Based Fungicidal and Bactericidal and Bactericidal Compositions, 1993). Applicant believes, in addition, that the generation of reactive oxygen species (ROS) by fixed copper compounds and the additional increase in ROS generation with the addition of an iron compound is pesticidal. Moreover, while not being limited held or bound of any particular theory or mechanism of action, it is thought that exudates on the surfaces of the plant leaves, taken together with the rainfall and the acidic rain, produce an acidic environment which dissolves the fixed copper compounds and releases free copper, which is very active against pathogens.

Thus without being limited, held or bound to these plant diseases disclosed, there are hundreds and hundreds of plant diseases amenable to control by copper pesticides and that the applicant's invention will surely potentiate the biocidal effects of copper pesticides against these pests. The composition of the present invention may be used with any known biologically inert carrier, including, but not limited to, a liquid diluent, e.g., water, a solid diluent and/or a surfactant. The composition of the present invention is designed to be compatible with the physical properties of copper hydroxide and any other active ingredients, method of application and environmental factors which may include soil type, moisture and temperature, organic matter, soil structure, current nutrient levels and more, well known to those in the chemical and agricultural art.

Moreover, without being limited held or bound to any particular theory or mechanism of action, the more iron added to the copper hydroxide or other fixed copper, the more biocidal/robust pesticide the invention will be toward pests.

Moreover, in one embodiment of the present invention herein, Applicant's iron doped copper hydroxide, or zinc doped copper hydroxide, or zinc and iron doped copper hydroxide, in an optional embodiment, may be stabilized or overcoated. U.S. Pat. No. 4,404,169 Ploss, et al, discloses methods of stabilizing compounds of the applicant's invention. Overcoating, can modulate release of the active ingredient.

In an alternate embodiment, insoluble iron compounds, such as iron hydroxide or iron oxyhydroxide, may be added to copper hydroxide so that there are two separate components. In a further alternate embodiment, iron hydroxide or other insoluble iron compounds, may be added to the iron doped copper hydroxide, so there are also two separate components. In each case, everything goes together in the spray tank for agricultural uses.

Moreover, since iron and copper are recognized micronutrients, recognized by the American Society of Agronomy and the Soil Science Society of America, then it follows that the remaining micronutrients boron, chloride, manganese, molybdenum and zinc, can easily be added to the iron or zinc or iron and zinc doped copper hydroxide, which uses iron and or zinc as a dopant to produce a doped copper hydroxide iron fungicide/bactericide/nutrient with micronutrients for foliar, trunk, branch and/or root application and/or injection in the trunk or branches of the plant. Moreover, secondary nutrients such as calcium, magnesium and sulfur may also be added, singly or together in combination.

Applicant's invention is the only known foliar nutritional bactericidal formulation that enters the phloem and kills the HLB disease causing CandidatusLiberibacter (CLas) bacteria.

Since zinc has established anti-microbial activity against bacteria, fungi and other pathogens, Applicant proposes to potentiate, increase activity of the claimed iron doped copper hydroxide by further doping the copper hydroxide with a zinc compound so that the end product will be an iron doped, zinc doped copper hydroxide or other fixed copper. It is understood that the doping with zinc is provided by a zinc compound and not by the use of pure metallic zinc, an element.

Preferred embodiments of this invention include both a zinc compound doped copper hydroxide and an iron compound doped copper hydroxide. Zinc sulfate is an exemplary example of a zinc salt thought to be useful in the manufacture of compounds of the invention. The sulfur in zinc sulfate is also a plant nutrient. Applicant also claims copper hydroxide which is both doped with an iron compound and a zinc compound together. In the preparation of the iron doped copper hydroxide, excess iron more than that the copper hydroxide will incorporate, is left in the preparation, so that the upshot is iron doped copper hydroxide, with additional iron hydroxide, in the preparation thereof. It may very well be an iron oxyhydroxide or other iron compound incorporated in the doping process.

Iron doped copper hydroxide, with and without additional unincorporated iron hydroxide in the preparation, may be combined with zinc doped copper hydroxide with and without additional unincorporated zinc hydroxide or other zinc compounds, and both zinc and iron doped copper hydroxide with both additional unincorporated zinc and iron may also all be used in combinations or mixtures thereof. Other useful compounds are ferrites, which may be an additional alternate compound to be used stand alone, or may be combined as the iron and/or zinc doped copper hydroxide is also used. A ferrite is a type of ceramic compound composed of iron oxide ($Fe_2O_3$) combined with one or additional metallic elements in chemical combination. See Encyclopedia Britannica. See Wikipedia. Exemplary examples are copper zinc iron oxide ($CuZnFe_2O_4$). See Sigma order confirmation, order date Apr. 6, 2015, order number 3013972345. This order also contains a copper iron oxide ferrite ($CuFe_2O_4$). See Sigma Technical Services answer of Jeanne Harrell, "*X-ray Diffraction Results*", dated Apr. 14, 2015. Other ferrites include zinc iron oxide nanopowder ($ZnFe_2O_4$). See American Elements 150416RP03, dated Apr. 14, 2015. Another ferrite is a copper ferrite ($CuFe_2O_4$). See American Elements data sheet for copper ferrite, dated Apr. 16, 2015. There may be manganese in the composition of useful ferrites. While not being limited, held or bound, the aforesaid ferrites are exemplary examples thought to be useful in the practice of the invention, and may be combined in any combination with themselves or other compounds previously disclosed in the practice of the invention. Preferably, the size of the ferrites are from 0.5 nm up to 30 microns.

These combinations or mixtures thereof are easily tested against bacteria, fungi, viruses, mycoplasma and other pathogens, by rapid, well established, routine testing well known to those skilled in the art, such as laboratory high throughput screening of vast numbers of compounds in vitro, and/or greenhouse plantings.

The compositions of the Applicant's invention are especially directed and exquisitely suited as a treatment for Huanglongbing (HLB) disease of citrus, and citrus canker, and other citrus diseases, such as Greasy Spot, Melanose, and Alternaria Brown Spot, where copper is currently utilized. Applicant's doped composition of fixed coppers doped with zinc, iron, or both, are also useful in treating banana plants afflicted with Black Sigatoka disease, Yellow Sigatoka disease and Panama disease.

Moreover, the small size of Applicant's invention will improve foliage coverage of leaves, which is well known in the art, that small particulates provide more uniform and superior coverage to leaves of plants. A critical and distinguishing feature of the Applicant's invention is that in preferred embodiments it can be an ultra-small insoluble copper and iron compound. Moreover, another critical aspect of Applicant's invention is the size of Applicant's iron doped copper hydroxide such that it is enabled for systemic uptake of the copper and iron. This size of Applicant's particles is unlike any size of any commercial fixed copper, so far as the Applicant is aware of, to facilitate systemic administration. Applicant's particulate at about 90+% particulate, is about 3.5 to 10 nm, as both a leaf protectorant and a systemic pesticide, and bactericide. Previous insoluble or fixed coppers are not systemic due to their large size for the most part. Applicant's particulate is about 90+% approximately 3.5 to 10 nm, in order to avoid aggregation, and has the best chance to facilitate systemic uptake. Preferably, Applicant's invention is to be administered with adjuvants/surfactants. Applicant's Transmission Electron Microscopy (TEM) image of FIG. 2 herein was tested with a surfactant, to insure good separation. Typical surfactants thought to be useful for the Applicant's invention are described in *Silwet Adjuvants and SAG Antifoams for Agricultural Applications*, (2012), published in Momentive publication of Momentive Performance Materials, Inc. of Albany, N.Y. and "*Adjuvants Products Guide*" of Nufarm.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention. Other fixed coppers may also be, joined, doped, with iron compounds and/or zinc compounds to practice the invention. Therefore, it is understood that Applicant's use of copper hydroxide for the fixed copper compound may be readily substituted with other known fixed copper compound. Copper hydroxide and other fixed coppers may be doped with insoluble iron compounds, and/or with insoluble zinc compounds.

Moreover, because of the ultra-small size of the doped components in the Applicant's invention, at approximately 3.5-10 nm, it has been shown that copper hydroxide plus the adjuvant/superspreader Silwet-77 is toxic to the Asian Citrus Psyllid nymphs, a vector of bacterial HLB. Applicant's invention, with the addition of zinc (Zn) and iron (Fe), is thought to further enhance the pesticide efficacy of copper hydroxide or other fixed coppers against this vector/carrier of HLB bacteria, and adult vector/carrier Psyllid nymphs.

The upshot is that doped components of the Applicant's invention hits the bacterial causes of HLB disease and Xyella fastidiosa infection of Olive Trees, and other external/internal plant pathogens in at least three ways at the least, as follows:

a) as a leaf protectorant with supra fine particle size; i.e. 3.5-10 nm;

b) as a leaf and systemic pesticide bactericide/fungicide; i.e. 3.5-10 nm; and, c) as a pesticide against vector/carrier of HLB bacteria, the Asian Citrus Psyllid nymphs and adults, and sharpshooters, froghoppers, and spittlebugs, vectors of XyellaFastidosa. Additionally, Applicant's invention simultaneously treats citrus canker and other citrus diseases.

In one embodiment of the present invention, the doped component is a fixed copper compound doped with magnesium and/or calcium.

Moreover, compounds of the Applicant's invention may be used with agents which currently synergizes with copper administration, such as for example Regalia biofungicide, and horticultural oils, and pesticidal adjuvants such as Silwet-L77, and other pesticides.

Compounds of the present invention are suitable for the customary adjuvants and formulation aids, which include but not limited to surfactants, wetting agents, stabilizers, dispersants and anti-foam agents.

Applicant claims iron compounds doped into copper hydroxide preferably iron hydroxide or iron oxide, zinc compounds doped into copper hydroxide preferably zinc oxide, iron compounds and zinc compounds doped together in copper hydroxide. These doped copper hydroxide compounds may be combined in any combination, or mixtures thereof and additional iron compounds, e.g. iron hydroxide, or zinc compounds, e.g. zinc oxide, may be added. For example, iron hydroxide doped copper hydroxide at 15 at % iron may have free unincorporated iron hydroxide with it at 5, 10, 15, 20, 25, 30, 35 at % iron hydroxide or more together with the 15 at % iron hydroxide doped copper hydroxide. Applicant claims all fixed copper compounds doped with iron compounds and/or zinc compounds for agricultural pesticidal usage.

EXAMPLES

The following examples illustrate the invention without limiting it. Except where otherwise indicated, the parts and percentages shown are expressed by percentage (at %).

Example 1

Synthesis of Iron-Doped Copper Hydroxide

Iron-doped Copper Hydroxide (Fe—Cu(OH)$_2$) composite powder is synthesized using a wet chemical process. The starting materials for the synthesis were copper nitrate hexahydrate(Cu(NO$_3$)$_2$.6H$_2$O), iron chloride (FeCl$_3$), sodium hydroxide (NaOH) and deionized water (H$_2$O). To synthesize ~15 at % Fe-doped-Cu (OH)$_2$, 2.43 g of copper nitrate hexahydrate and 0.4 g of iron chloride were dissolved in 75 mL of deionized water in a round bottom flask. The solution was refluxed for 3 hours. Once the solution cooled down to room temperature, 102.2 mL of 0.25 M NaOH was added. The pH at this stage was between 10 and 11. Subsequently, the solution was transferred to a beaker and another 102.2 mL of NaOH was added, while stirring the solution, using a high shear mixer at ~1000 rpm. The pH after the addition of NaOH was between 11 and 12. The precipitate was washed one time using deionized water and finally dried in air. Similar methods were used to synthesize iron-copper hydroxide composite, where the amount of iron was varied from 20 to 50 at %.

Figure 2:
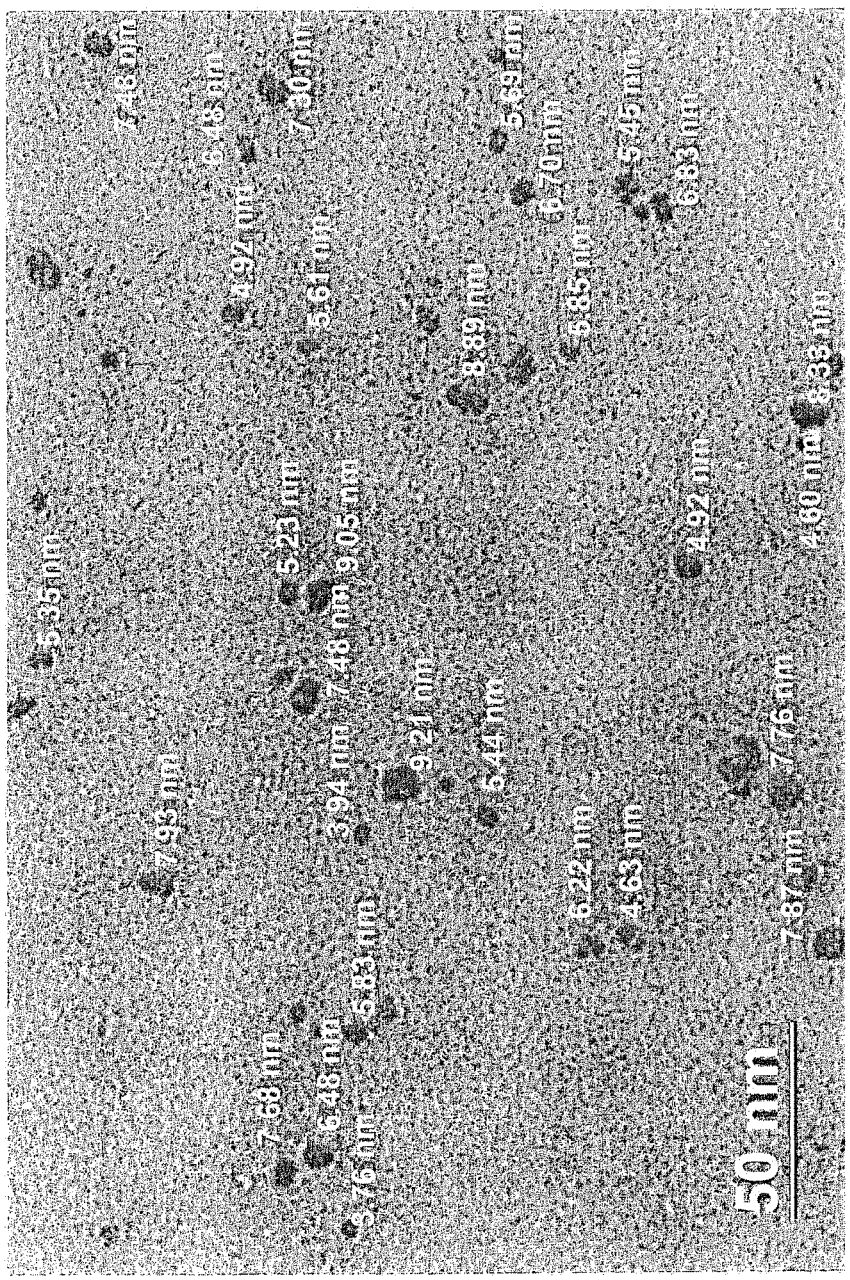
FIG. 2 is a transmission electron microscopy (TEM) image of Applicant's iron doped copper hydroxide at 15 at % iron in accordance with one embodiment of the present invention. The scale on the lower left of FIG. 2 shows a comparable length of 50 nm. The size of the iron doped 15 at % Fe copper hydroxide particulates is about 3.5 nm to 9 nm, tested in quadruplicate and by transmission electron microscopy (TEM).
Figure 3:
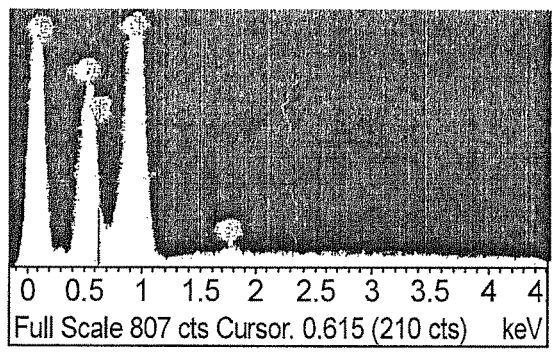
FIG. 3 is an elemental analysis chart demonstrating the presence of both iron and copper in the iron doped copper hydroxide compound in accordance with one embodiment of the present invention of FIG. 1 and FIG. 2 above.
Figure 3:
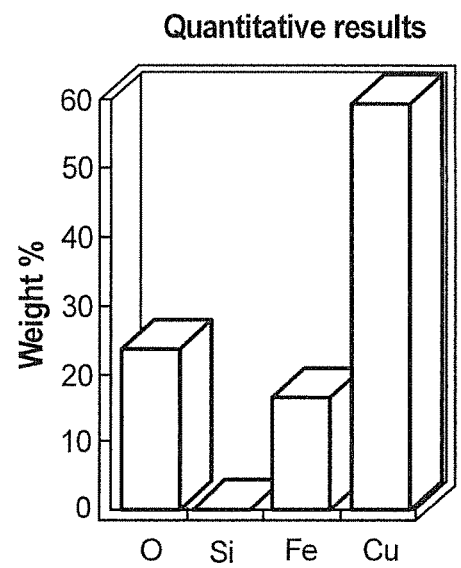
Figure 4:
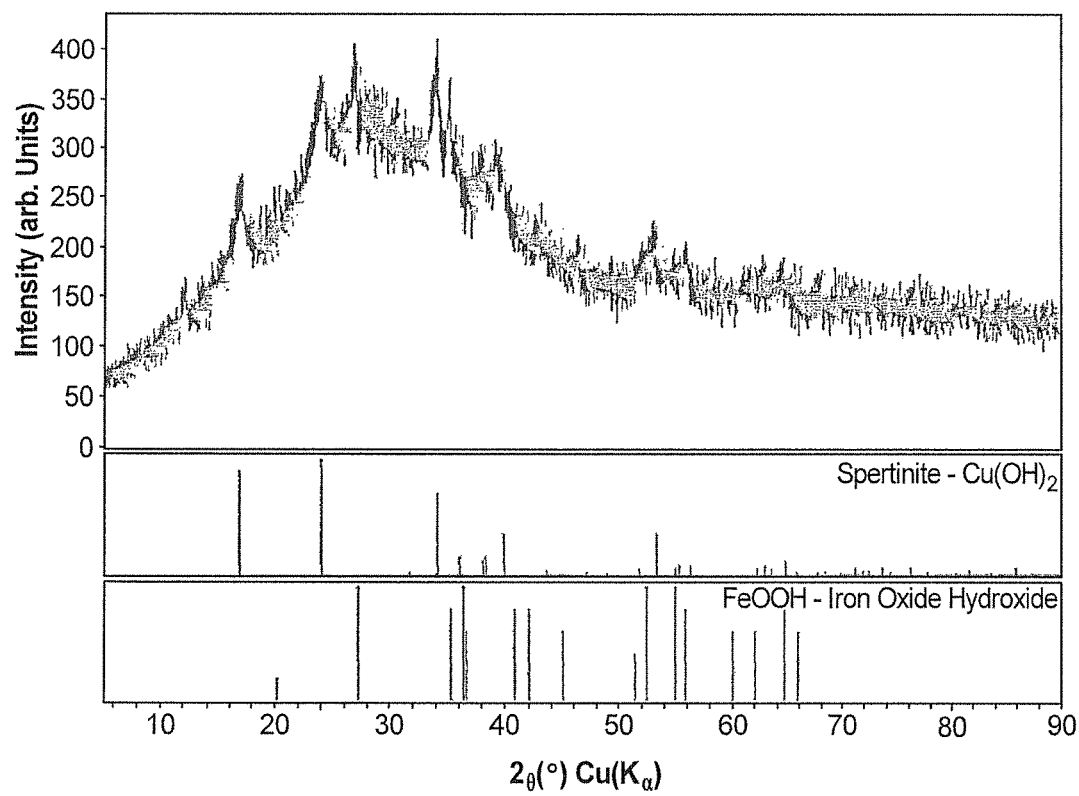
FIG. 4 is the X-ray diffraction of 15 at % iron doped copper hydroxide with an additional 10 at % iron that the copper hydroxide is unable to incorporate, so that the final composition is 15 at % iron doped copper hydroxide +10 at % unincorporated/free iron hydroxide and/or iron oxide.

FIG. 1 is an X-ray diffraction test verifying that copper hydroxide is doped with an insoluble iron. In connection therewith, in FIG. 2 herein, Applicant submits a data sheet of Applicant's iron doped copper hydroxide with 15 at % iron elemental analysis of FIG. 3. FIG. 2, discloses Applicant's invention tested out by TEM at about 90%+particulates, which is a very narrow particulate distribution unlike any other commercial product, between 3.5 nm and 10 nm. FIG. 4 is the X-ray diffraction of 15 at % Iron doped+ additional 10 at % Iron that the copper hydroxide is unable to incorporate, so that the final preparation is 15 at % Iron doped copper hydroxide+10 at % unincorporated/free Iron Hydroxide and or Iron Oxide.

Example 2

Synthesis of Iron-Zinc-Doped Copper Hydroxide

Iron-Zinc-doped Copper Hydroxide (Fe—Zn—Cu (OH)$_2$) composite powder is synthesized using a wet chemical process. The starting materials for the synthesis is copper nitrate hexahydrate (Cu(NO$_3$)$_2$.6H$_2$O), iron chloride (FeCl$_3$), zinc sulfate heptahydrate (ZnSO$_4$.7H$_2$O), sodium hydroxide (NaOH) and deionized water (H$_2$O). To synthesize ~7.5 at % Fe-7.5 at % Zn-doped-Cu(OH)$_2$, 2.43 g of copper nitrate hexahydrate, 0.21 g of zinc sulfate heptahydrate and 0.19 g of iron chloride is dissolved in 75 ml, of deionized water in a round bottom flask. The solution is refluxed for 3 hours. Once the solution cools down to room temperature, 102.2 mL of 0.25 M NaOH is added. Subsequently, the solution is transferred to a beaker and another 102.2 mL of NaOH is added, while stirring the solution, using a high shear mixer at ~1000 rpm. The precipitate is washed one time using deionized water and finally dried in air. The similar method is used to synthesize other variations of iron-zinc-copper hydroxide composite.

Example 3

Synthesis of Zinc-Doped Copper Hydroxide

Zinc-doped Copper Hydroxide (Zn—Cu(OH)$_2$) composite powder is synthesized using a wet chemical process. The starting materials for the synthesis is copper nitrate hexahydrate (Cu(NO$_3$)$_2$.6H$_2$O), zinc sulfate heptahydrate (ZnSO$_4$.7H$_2$O), sodium hydroxide (NaOH) and deionized water (H$_2$O). To synthesize ~15 at % Zn-doped-Cu(OH)$_2$, 2.43 g of copper nitrate hexahydrate, 0.42 g of zinc sulfate heptahydrate is dissolved in 75 mL of deionized water in a round bottom flask. The solution is refluxed for 3 hours. Once the solution cools down to room temperature, 102.2 mL of 0.25 M NaOH is added. Subsequently, the solution is transferred to a beaker and another 102.2 mL of NaOH is added, while stirring the solution, using a high shear mixer at ~1000 rpm. The precipitate is washed one time using deionized water and finally is dried in air. The similar method is used to synthesize other variations of zinc-copper hydroxide composite. The Applicant preferably has used additional zinc sulfate heptahydrate, so that the finished synthesis contains zinc doped copper hydroxide plus unincorporated zinc oxide alone, in the finished preparation.

Use of Compositions for Treating Black Sigatoka disease, Yellow Sigatoka Disease and Panama Disease in Banana Crop Plants:

The Applicant's agricultural pesticides used to treat agricultural crops affected with vascular crop diseases such as Huang-longbing bacterial disease in orange crop plants or Xylella fastidosa disease in olive tree crop plants, namely with zinc or iron-doped copper hydroxide singly or together, and/or with ferrites, are exquisitely also suited for fungal diseases of banana, especially the three leading banana killers worldwide, namely Black Sigatoka disease, Yellow Sigatoka disease and Panama disease.

Bananas are a staple for an excess of 400 million subsistence people in the tropics. They are under vicious critical attack by these fungal diseases. See Mourichon et al, Sigatoka Leaf Spot Diseases, PROMUSA Working Group, International Network for Improvement of Banana and Plantain Montpellier Cedex, FR, www.biodiversityinternational.org/uploads/tx_news/Sigatoka_leaf_spot_diseases_699.pdf, October, 1997, which discusses Black Sigatoka disease, also known as Black Leaf Streak disease (BLSD) caused by the ascomycetous fungi *Mycosphaerella fijiensis* Morelet, as well as Yellow Sigatoka disease, also known as Sigatoka disease (SD), caused by the ascomycetous fungi *M. musicola* Leach×Mulder. Mourichon et al also discuss the fact that systemic topical spraying of fungicides is a cause of environmental concern, and that the fungi grow resistant to conventional fungicides. See Ramaker, "*Banana disease continues to Spread*", resource.wageningenur.nl, Nov. 26, 2015, showing aerial photos depicting widespread destruction of banana plants in a banana plantation. Ramaker states that there is widespread destruction of banana plants in the Middle East, Southeast Asia, East Africa and Australia affected by Panana disease of banana plants. Ramaker also states it is only a matter of time before it spreads to South America. Ramaker notes that efforts to quarantine afflicted banana plants have failed to stop the spread of Panama disease in banana plants. Ramaker notes that the Panana disease causing fungus *Fusarium oxysorum* survives in the soil for long periods of time, even after afflicted banana plants are removed. See "Banana Cultivation" of Wageningen; see "*Black Sigatoka of Banana: The most important disease of a most important fruit*" of Randy Ploetz. Black Sigatoka is the most important banana disease, opus cited, see "*Plant Health Australia Fact Sheet*." See also Outrageous Minds publication article, "*Banageddon: Millions face hunger as Panama disease and Black Sigatoka decimate global banana crop*" and see also "*Black Sigatoka: An Increasing Threat to Banana Cultivation*" Douglas H Marin, et al.

Black Sigatoka is currently being treated with systemic fungicides which are failing. See Douglas H. Marin et al. Opus cited. In a personal communication with one of the authors above, Turner Sutton discloses "Copper fungicides have been used for Sigatoka control, especially in the past there was a heavy use of Bordeaux mixture followed by other copper based formulations. Because of the heavy use of copper in the past it accumulates in the soil at phytotoxic levels. This, and the development of new protectant products discouraged the use of Copper fungicides. Additionally, with the introduction of agricultural oil, some copper formulations react with the oil causing phytotoxicity on the leaves." As this article discloses these systemic fungicides are becoming inactive due to mutations and chemical resistance. This has only gotten worse since the time of the article in 2003. See "Black Sigatoka" by Randy Ploetz, which discloses that fixed coppers were the old standard methods until the systemic fungicides, beginning with Benomyl. Resistance has developed with these systemics with challenges ahead for control of Black Sigatoka disease in banana crops. According to Mourichon et al, supra, Yellow Sigatoka disease is also prone to pesticide resistance. Because of the wet conditions where bananas are grown (see Table 1, Randy Ploetz in "*Disease Control*"), this has necessitated up to about 50 sprayings weekly, with costly environmental damage, labor and capital intensive administration of these fungicides, which adds about 25% to the cost of banana production see "*Top Banana*" at Martinez page 5.

"*Copper completes the circle for Sigatoka control*" by Terry Mabbett, which discloses that "Copper fungicide has travelled the complete circle in the control of Sigatoka disease on banana. Copper was the very first fungicide to be used against yellow Sigatoka over 60 years ago and is now back in contention and favour due to its broad spectrum activity and long history of use without resistance which now plagues many single-site systemic fungicides." See Mabbett also "Copper makes a full circle" at page 221, and "*Positive profile for copper fungicide*" on page 221, and "*Rise and fall of systemic fungicides*" at page 222.

It is further noted that all existing fixed copper fungicides are "crop protectants" and do not enter the systemic vascular circulation of the banana plant, and therefore are inactive after a banana plant has become infected. The fixed copper fungicides as crop protectants kill this Sigatoka Disease fungus spore on the leaf and block its entry through the stoma into the leaf. See Bennett et al, Black Sigatoka of Bananas and Plantains, p. 6, Cornell University, www.apsnetorg/edcenter/intropp/lessons/fungi/ascomaycetes/Pages/BlackSigatoka.aspx, 2003.

In contrast to known fungicides, Applicant's invention with its preferred 5-10 nm size will enter the banana leaf through the stoma, or by other means, which is referred to being "locally systemic", to counter the fungus systemically affecting the afflicted banana plant. Simultaneously, the compositions of Applicant's invention act like other classical fixed coppers, as a crop protectant on the surface of the leaf. Moreover, the compositions of Applicant's invention is used to reduce the number of sprayings due to wet weather, because of its systemic activity like the prior systemics, which were unsuccessfully used to try and control Black Sigatoka disease or Yellow Sigatoka disease in banana plants. Moreover, as Ploss, in U.S. Pat. No. 7,105,136B2, has shown in his '136 patent, inferentially, because of the systemic activity of nano copper hydroxide in using Applicant's fungicidal compositions, only a fraction of the quantity of the previously used copper hydroxide will be needed, to be effective.

Moreover the Applicant's supercharging by doping of copper hydroxide, copper oxide or other fixed coppers, with zinc or iron, or both, further strikingly increases functional activity and reduces copper usage, thus further mitigating the harmful effects of excess copper accumulation in the soil. Moreover both the iron and zinc are recognized established micronutrients to simultaneously feed the banana plant.

The Applicant notes that "*Pesticides Registered for Use in Banana in Hawaii*" of EPA reg. no. Sep. 2, 2014, Hawaii Department of Agriculture Pesticides Branch; National Pesticide Information Retrieval System (NPIRS) Purdue University, shows ten different prior art copper hydroxide formulations, which were approved to treat Black and Yellow Sigatoka in bananas plus another five copper formulations. However, every one of those ten prior art different copper hydroxide formations, is a crop protectant with particles too big to enter the leaf site of infection, and therefore are incapable of being systemic in the vasculature of the banana plant. In "*Control of black Sigatoka disease: Challenges and Prospects*" by Ebimieowei Etebu, at page 510, Etebu states as follows: "Protectants were the first group of fungicides that were discovered and used in crop protection. They are non systemic, and as such do not penetrate plant tissue. Protectant fungicides do not control fungi that are already established within the plant tissues since they do not penetrate the plant tissues themselves."

The Applicant's fungicidal compositions are distinguished from the prior art by their unique doping with zinc and/or iron, singly or together, and with a unique small size, capable of entering the banana plant leaf, the site of infection.

Panama disease s another blight affecting afflicted banana plants. Panama disease is caused by a fungus *Fusarium oxysporum* fsp. cubense (Foc), which, along with *Black Sigatoka* are the two grievous existential threats to banana crop production and the lifeblood of over 400 million subsistence banana crop farmers. Panama disease is a vascular fungus which can remain active in the soil for many decades and it cannot be fully controlled by prior art fungicides. There is a desperate need for treatment for Panama disease. See "*YES WE HAVE NO BANANAS: The world's favorite fruit is slowly but surely being driven to extinction*" by Gwynn Guilford in Quartz; See also "*Yes! We have no bananas? It could actually happen*" Mark Koba; see "*Fungus Threatens Banana Supply*" Mark Koba; see also "*Worse Comes to Worst: Bananas and Panama Disease-When Plant and Pathogen Clones Meet*" Nadia Ordonez in PLOS Pathogens.

Applicant's fungicidal compositions, with their small size suitable for systemic uptake, in the banana plant, and the proven anti-fungal characteristics of the fixed coppers i.e. copper hydroxide, plus being doping with iron and/or zinc, make Applicant's compositions very desirable for the treatment of Panama disease.

Moreover, fixed coppers, i.e. copper hydroxide, are approved for many other banana diseases, i.e. Black pitting, see "*Pesticides Registered for Use in Banana in Hawaii*" (Sep. 2, 2014). In point of fact, copper hydroxide is recommended for "*Bananas, Beans, Cabbage, Cacao, Carrots, Cauliflower, Celery, Citrus, Coffee, Cucumber, Grapes, Onion, Peas, Peanuts, Pepper, Potato, Rice, Tomato and Watermelon*" see "*Fungicides*" Jocanima Corporation. In fact, copper is approved in dozens of plant diseases, bacteria, fungi and viruses, see Denis Rusjan (2012). "*Copper in Horticulture, Fungicides for Plant and Animal Diseases*", Dr. Dharumadurai Dhanasekaran (Ed.). pp. 257-278.

However, despite the limited success of the aforementioned copper based treatments for treating banana crop plants afflicted with Black Sigatoka disease, Yellow Sigatoka disease, or Panama disease, in contrast, Applicant's doped fixed coppers compositions, which are doped with zinc, or iron, or both, or, alternatively, Applicant's ferrite compositions, are uniquely capable of systemically or effectively capable of treating banana crop plants afflicted with "Panama" disease, "Yellow Sigatoka" disease and "Black Sigatoka" disease, while minimizing the accumulation of copper in crop soils.

Although the present invention has been disclosed in terms of a preferred embodiment, it is further known that other modifications may be made to the present invention, without departing from the spirit and scope of the invention.

I claim:

1. A method of applying a pesticide composition to banana crop plants, wherein said composition is effective in treating banana plants afflicted with Black Sigatoka disease, Yellow Sigatoka disease and Panama disease, and said composition comprises:
   a) at least one biologically inert carrier; and
   b) at least one doped component comprising at least one fixed copper compound comprising copper oxide or copper hydroxide doped with at least one compound selected from the group consisting of iron compounds, zinc compounds and combinations thereof;
   said is effective in controlling Black Sigatoka disease, Yellow Sigatoka disease and Panama disease in the banana crop plants.

2. The method according to claim 1, wherein at least one fixed copper compound is doped with at least one iron compound.

3. The method according to claim 1, wherein said at least one fixed copper compound is doped with at least one zinc compound.

4. The method according to claim 1, wherein said fixed copper compound further comprises a component selected from the group consisting of cupric hydroxide, copper oxychloride, copper oxide, cupric carbonate basic, copper sulfate basic, tribasic copper sulfate, cuprous oxide, cupric citrate, cupric phosphate, cuprobam, indigo copper, minerals brochantite, langite, malachite, cornetite, libethenite, pseudolibethenite, pseudo-malachite, antlerite, covellite, marshite, cuprite, chalcocite, Rogojski's salt, brochantite, hydrocyanite, nantokite, dolerophane, ammonia copper carbonate, basic copper chloride, and combinations thereof.

5. The method according to claim 1, wherein said iron compound is an insoluble or a substantially insoluble iron compound.

6. The method according to claim 5 wherein said iron compound is selected from the group consisting of iron hydroxide, iron oxyhydroxide, iron oxide, iron glucose, ferric citrate, Ferritin, ferrous fumarate and ferrous sulfate.

7. The method according to claim 1, wherein said zinc compound is an insoluble or a substantially insoluble zinc compound.

8. The method according to claim 7, wherein said zinc compound is selected from the group consisting of zinc hydroxide and zinc oxide.

9. The method according to claim 1, wherein said iron compound is iron oxide, iron hydroxide and/or iron oxyhydroxide.

10. The method according to claim 1, wherein said doped component includes about 15 atomic percentage (at %) iron from said iron compound doped within said fixed copper compound.

11. The method according to claim 1, wherein particle size of doped component is about 0.5 nm to 30 microns.

12. The method according to claim 1, wherein said iron compound is at least one insoluble or a substantially insoluble iron compound.

13. The method according to claim 1, wherein said iron compound is at least one insoluble or a substantially insoluble iron compound, and wherein said iron compound is iron hydroxide or iron oxide.

14. The method according to claim 1, further comprising at least one zinc compound mixed with a) and b).

15. The method according to claim 14 wherein said at least one zinc compound is an insoluble or a substantially insoluble zinc compound.

16. The method according to claim 15, wherein said at least one zinc compound is zinc hydroxide or zinc oxide.

17. The method according to claim 1, wherein said pesticide composition is a plant nutritional composition.

18. The method according to claim 1, wherein said pesticide composition is administered to said banana plant crops by dusting, sprinkling, spraying, brushing, dipping, smearing, impregnating, injection of the composition into plant vasculature or application to a root system.

* * * * *